US012042476B2

(12) United States Patent
Igdoura et al.

(10) Patent No.: US 12,042,476 B2
(45) Date of Patent: Jul. 23, 2024

(54) METHODS FOR THE TREATMENT OF LYSOSOMAL STORAGE DISEASES

(71) Applicant: McMaster University, Hamilton (CA)

(72) Inventors: Suleiman Igdoura, Dundas (CA); Fiona Weaver, Hamilton (CA); Richard Austin, Ancaster (CA); Colin Nurse, Dundas (CA)

(73) Assignee: MCMASTER UNIVERSITY, Hamilton (CA)

( * ) Notice: Subject to any disclaimer, the term of this patent is extended or adjusted under 35 U.S.C. 154(b) by 0 days.

(21) Appl. No.: 18/106,290

(22) Filed: Feb. 6, 2023

(65) Prior Publication Data
US 2023/0277485 A1    Sep. 7, 2023

Related U.S. Application Data

(60) Provisional application No. 63/306,741, filed on Feb. 4, 2022.

(51) Int. Cl.
| | | |
|---|---|---|
| *A61K 31/192* | (2006.01) | |
| *A61K 9/00* | (2006.01) | |
| *A61K 45/06* | (2006.01) | |
| *A61P 3/00* | (2006.01) | |

(52) U.S. Cl.
CPC .......... *A61K 31/192* (2013.01); *A61K 9/0053* (2013.01); *A61K 45/06* (2013.01); *A61P 3/00* (2018.01)

(58) Field of Classification Search
CPC .... A61K 31/192; A61K 9/0053; A61K 45/06; A61P 3/00
See application file for complete search history.

(56) References Cited

U.S. PATENT DOCUMENTS

| | | |
|---|---|---|
| 2017/0044590 A1 | 2/2017 | Haldar et al. |
| 2021/0177867 A1 | 6/2021 | Cohen et al. |
| 2021/0186990 A1 | 6/2021 | Cohen et al. |

FOREIGN PATENT DOCUMENTS

| | | | |
|---|---|---|---|
| WO | 0053174 A1 | 9/2000 | |
| WO | 2006059237 A1 | 6/2006 | |
| WO | WO-2015042326 A2 * | 3/2015 | ............... C12Q 1/34 |
| WO | WO-2016081365 A1 * | 5/2016 | ............. A61K 31/07 |

OTHER PUBLICATIONS

Ozcan, Umut, et al. "Chemical Chaperones Reduce ER Stress and Restore Glucose Homeostasis in a Mouse Model of Type 2 Diabetes." Science, vol. 313, No. 5790, Aug. 2006, pp. 1137-1140. DOI.org (Crossref), https://doi.org/10.1126/science.1128294. (Year : 2006).*

(Continued)

*Primary Examiner* — Clinton A Brooks
*Assistant Examiner* — Kyle Nottingham
(74) *Attorney, Agent, or Firm* — Bereskin & Parr LLP/S.E.N.C.R.L., s.r.l.; Luba Naiberger

(57) ABSTRACT

This application relates to the use of 4-phenylbutyric acid, as well as pharmaceutically acceptable salts, co-crystals, polymorphs, solvates, analogs and/or pro-drugs thereof for the treatment of lysosomal storage disease, in particular gangliosidoses such as Tay Sachs disease (TSD) and Sandhoff disease (SD), alone, or in combination with other compounds and/or treatments.

16 Claims, 20 Drawing Sheets

Specification includes a Sequence Listing.

(56) References Cited

OTHER PUBLICATIONS

Wei, Hui, et al. "ER and Oxidative Stresses Are Common Mediators of Apoptosis in Both Neurodegenerative and Non-Neurodegenerative Lysosomal Storage Disorders and Are Alleviated by Chemical Chaperones." Human Molecular Genetics, vol. 17, No. 4, Feb. 2008, pp. 469-477. (Year: 2008).*

"Lipid Storage Diseases." NINDS Catalog, Jun. 1, 2018, https://catalog.ninds.nih.gov/publications/lipid-storage-diseases. (Year: 2018).*

"Rationalizing Combination Therapies." Nature Medicine, vol. 23, No. 10, Oct. 2017, pp. 1113-1113. www.nature.com, https://doi.org/10.1038/nm.4426. (Year: 2017).*

Delnooz, C. C. S., et al. "New Cases of Adult-Onset Sandhoff Disease with a Cerebellar or Lower Motor Neuron Phenotype." Journal of Neurology, Neurosurgery, and Psychiatry, vol. 81, No. 9, Sep. 2010, pp. 968-972. PubMed, https://doi.org/10.1136/jnnp.2009.177089. (Year: 2010).*

Xiao, Changrui, et al. "Sandhoff Disease." GeneReviews®, edited by Margaret P. Adam et al., University of Washington, Seattle, 1993. PubMed, http://www.ncbi.nlm.nih.gov/books/NBK579484/. (Year: 2022).*

Wei et al., "ER and oxidative stresses are common mediators of apoptosis in both neurodegenerative and non-neurodegenerative lysosomal storage disorders and are alleviated by chemical chaperones", Human Molecular Genetics, 2008, vol. 17, No. 4, 469-477.

Pereira et al., "Tuning protein folding in lysosomal storage diseases: the chemistry behind pharmacological chaperones", Chemical Science, 2018, 9, 1740-1752.

* cited by examiner

FIGURE 4
hexb[+/+]    hexb[-/-]
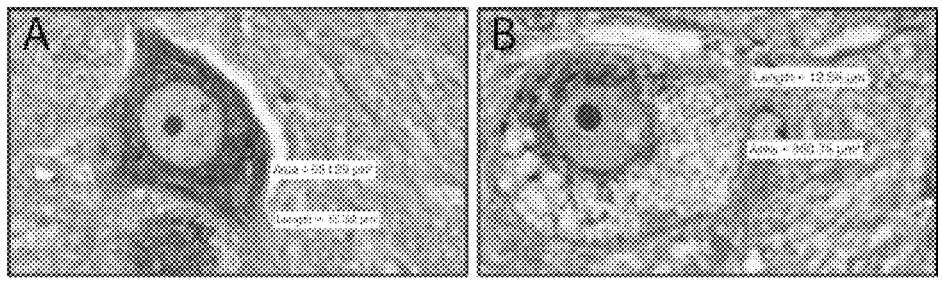
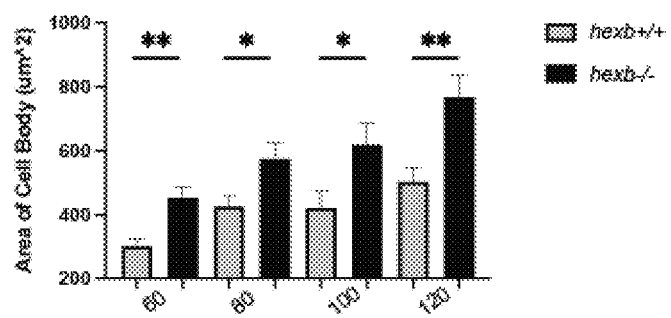
C  Cell Body Area of Anterior Horn Neurons
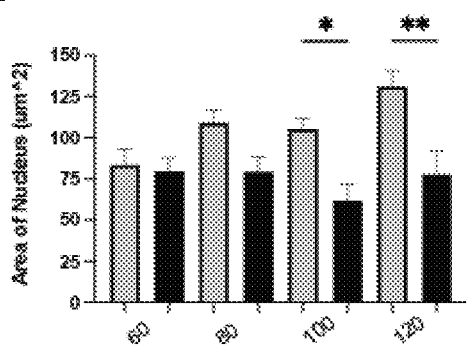
D  Nuclear Area of Anterior Horn Neurons
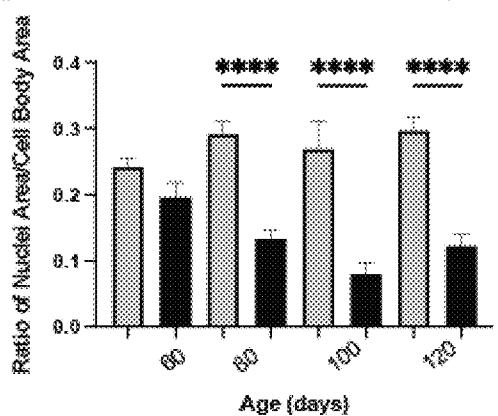
E  Ratio of Nuclei Area to Cell Body Area
Age (days)

METHODS FOR THE TREATMENT OF LYSOSOMAL STORAGE DISEASES

CROSS-REFERENCE TO RELATED APPLICATIONS

The present application claims the benefit of priority from U.S. provisional patent application No. 63/306,741 filed on Feb. 4, 2022, the contents of which are incorporated by reference in their entirety.

INCORPORATION OF SEQUENCE LISTING

A computer readable form of the Sequence Listing "3244-P67474US01_SequenceListing.xml" (3,709_bytes), submitted via Patent Center and created on Feb. 8, 2023, is herein incorporated by reference.

FIELD

The present application relates to the use of compounds that mitigate ER stress pathway for the treatment of lysosomal storage disease, alone, or in combination with other pharmaceuticals.

BACKGROUND

Lysosomal storage diseases (LSDs) represent a major challenge for the health care system with a frequency of about 1/8000 live births. GM2 gangliosidoses are a group of rare, recessively inherited metabolic LSDs that include Tay Sachs disease (TSD) and Sandhoff disease (SD) [1]. Both diseases have a variety of forms depending on the specific mutations involved and the remaining residual enzymatic activity. SD consists of infantile, juvenile, and late-onset forms. Tay Sachs and Sandhoff diseases (TSD and SD) are fatal by age 3-5 years due to progressive neural degeneration caused by intralysosomal accumulation of GM2 ganglioside. Tay-Sachs disease is highly prevalent in Ashkenazi Jews and French Canadians, carrier frequencies 1/27 and 1/50 respectively, giving the disease some significance as a health issue. The Sandhoff mouse model (Hexb$^{-/-}$) more closely resembles the pathogenic process in TSD and SD in humans.

SD and TSD can present with a multiplicity of symptoms including cognitive and speech impairments, ataxia, and lower motor neuron disease [1, 2]. Late-onset SD has been reported in an array of clinical case reports as presenting as a motor neuron disease such as spinal muscular atrophy and amyotrophic lateral sclerosis [2-9]. Lower motor neuron disease is prevalent in 42% of late onset Sandhoff disease cases and has been described as one of the main clinical features [3]. Diffuse neuronal degeneration and enlarged neurons within the anterior horn of the spinal cord, which resembles the pathophysiology of lower motor neuron disease, has been reported in late-onset SD case studies [2, 8, 10, 11]. Hexb$^{-/-}$ mice, a model for SD disease, have severe accumulations of gangliosides and develop a disease phenotype. By 3 months of age these mice begin to present with severe motor deficits including impaired reflexes, muscle weakness and atrophy, ataxia, and tremors. Symptom onset is closely followed by death within about 4-6 weeks for a total lifespan of 4 months [12-14]. The pathophysiology and phenotypic display seen within these mice closely mimics that of SD and TSD, making this model significant in the examination and exploration of these fatal diseases.

The specificity of neuron population function correlates with the clinical features exhibited by late-onset Sandhoff disease patients. Clinical studies have reported wide-spread denervation that closely resembles the degeneration seen with lower motor neuron diseases, which connects functionally to symptomatic phenotypes such as muscle weakness and severe tremors [3, 10] [5-7, 15, 16]. The mechanisms of how the accumulation of GM2 results in the degeneration and death of motor neurons to produce symptoms are still being explored. Several hypotheses regarding the mechanisms behind the neurodegeneration seen in SD and TSD have been proposed, including lysosomal rupture, neuronal morphological changes, neuroinflammation, autophagy and mitochondria storage, and disruption of calcium homeostasis [17-22]. Although there is evidence for each of these, physiological conditions that cause endoplasmic reticulum (ER) stress thereby activating the unfolded protein response (UPR) and leading to apoptosis of neurons holds significant promise. ER stress has been linked to all the mechanisms proposed above, making it an ideal candidate for examination in these diseases [23].

In a recent study by Lu and colleagues, it was established that this dynamic ER remodeling seen within cells is actively driven by lysosomes [24]. Lysosomes were able to sense changes in the intracellular environment, such as metabolic changes, and repositioned accordingly in response to these alterations. This ultimately led to the redistribution of ER tubules and changes in the ERs global morphology [24]. This clearly demonstrates the tight interconnectivity that occurs between cellular organelles. ER can also interact with a multitude of other organelles, including the plasma membrane, mitochondria, peroxisomes, and Golgi, by forming membrane contact sites (MCSs) [25-28]. These contact sites allow the ER to communicate and coordinate with organelles to align their functions from which emerges a harmonized collection of functions that work in concert to maintain cellular homeostasis [28-30]. Since the ER has such a central role in protein synthesis, if any part of its network is disturbed it can initiate a series of events such as ER stress and the unfolded protein response which can result in cell death and disease.

In lysosomal storage diseases (LSD)s, lysosomal catabolism is severely inhibited which can affect a multiplicity of cellular functions including calcium homeostasis, autophagy, ER and mitochondrial function, which ultimately leads to apoptosis of cells and the phenotypic presentation of the disease. Tessitore and colleagues demonstrated that in a mouse model of GM1 gangliosidoses, mRNA levels of apoptotic associated factors such as CHOP, activated JNK, and activated caspase-12 were elevated in spinal cords of the knockout mice compared to wildtype. In addition, they showed that the diseased samples had more TUNEL positive cells scattered throughout the spinal cord in comparison to the wildtype [31]. Caspase activation has also been reported in LSDs. Specifically, in MPS II patient derived TD35 neuronal cultures, levels of caspase 3 and 7, which are both apoptotic executioner caspases, were significantly increased in comparison to controls [32]. A separate study by Sano et al, suggests a mechanism of $Ca^{2+}$ mediated apoptosis in which the accumulation of GM1 in a specific fractions of mitochondria-associated ER membranes alters $Ca^{2+}$ homeostasis and activates both ER stress mediated, and mitochondria evoked neuronal apoptosis [33]. Overall, current research indicates that chronic ER stress is prevalent and activation of the specific arms of the UPR has been shown in a variety of lysosomal storage diseases, including GM2 gangliosidoses [18, 31, 34-36].

Pereira and colleagues disclose the use of chaperones in LSDs, focusing on pharmacological chaperones (PCs), which according to Pereira, have the advantage of introducing selectivity in the form of a small molecule binding specifically to a given target. PCs are disclosed with reference to the treatment of Gaucher, Krabbe, GM1-gangliosidosis and other LSDs. Pereira does not disclose GM2-gangliosidosis or using 4-PBA to treat GM2-gangliosidosis, such as SD and TSD [60].

Wei and colleagues disclose the use of trimethylamine N-oxide dihydride (TMAO) and taurine-conjugated derivative, tauroursodeoxycholic acid (TUDCA) chaperons in GM1-gangliosidosis. GM2-gangliosidosis or the use of 4-PBA to treat GM2-gangliosidosis, such as SD and TSD is not disclosed by Wei [61].

At present, there is no effective treatment nor a cure for lysosomal storage diseases such as Sandhoff or Tay-Sachs. Therefore, there is a critical need for any effective treatments to prevent or slow the progression of these diseases.

The background herein is included solely to explain the context of the disclosure. This is not to be taken as an admission that any of the material referred to was published, known, or part of the common general knowledge as of the priority date.

SUMMARY

The present disclosure describes methods for the treatment of lysosomal storage disease (LSD) based on therapeutic targets involved in ER stress and unfolded protein response (UPR), which not only may extend patient life spans by years but also improve quality of life. Sandhoff mice demonstrated significant upregulation of several ER stress markers in motor neurons that appeared to coincide with significant lysosomal accumulation. In addition, sequential and age-dependent expression changes in ATF6 and CHOP and their prominent nuclear localization within anterior horn motor neurons were observed. Markers of apoptosis, caspases and PARP also appeared to be activated in spinal cords of Sandhoff mice starting as early as 60 days. More than 50% reduction in neuronal numbers was noted in all regions of the spinal cord of Sandhoff mice between ages 80 and 120 days. Administration of 4-phenylbutyric acid (4-PBA), that mitigates ER stress at 40 days of age resulted in significant improvement in motor neuromuscular function and life span in Sandhoff mice in comparison to untreated controls.

In accordance with an aspect of the present application, there is provided a method of treating a lysosomal storage disease (LSD) comprising administering a therapeutically effective amount of 4-phenylbutyric acid (4-PBA), or a pharmaceutically acceptable salt, co-crystal, polymorph, solvate, analog and/or pro-drug thereof, to a subject in need thereof.

In an embodiment, the lysosomal disease is GM2 gangliosidoses.

In an embodiment, the GM2 gangliosidoses is selected from Tay Sachs disease (TSD) and Sandhoff disease (SD).

In an embodiment, the SD is selected from infantile, juvenile, and late-onset forms.

In an embodiment, the method of the present application achieves at least one of delayed neurological symptoms, reduced pain, improved motor neuromuscular function or increase life span.

In an embodiment, 4-PBA is administered orally.

In an embodiment, 4-PBA is administered at a dose ranging from about 0.1 g/kg body weight/day to about 10 g/kg body weight/day.

In accordance with an aspect of the present application, there is provided a method of treating a patient having a lysosomal storage disease; the method comprises administering to a patient a therapeutically effective amount of a small molecule chaperone containing an active ingredient that inhibits a target within the neurodegeneration-mediated unfolded protein response (UPR) pathway.

In an embodiment, treatment results in increased life span, reduced pain, delayed neurological symptoms and improved motor neuromuscular function.

In an embodiment, the target comprises one or more of caspase 7, Activating Transcription Factor 6 (ATF6), Poly (ADP-ribose) polymerase (PARP), C/EBP Homologous Protein (CHOP), XBP1 (X-Box Binding Protein 1), Glucose Regulatory Protein 78 (Grp78), Protein disulfide isomerase (PDI).

In an embodiment, the small molecule chaperone comprises but is not limited to 4-phenylbutyric acid (4-PBA) or a derivative thereof, a general inhibitor of caspases such as Emricasan, and/or a grp78 antagonist.

In an embodiment, 4-PBA is repurposed for the treatment of a lysosomal storage disease.

In an embodiment, the small molecule chaperone is administered in combination with currently available treatments for lysosomal storage diseases.

In an embodiment, the lysosomal storage disease comprises infantile and juvenile Sandhoff disease (SD) or Tay Sachs disease (TSD).

In an embodiment, the lysosomal storage disease comprises a late-onset Sandhoff disease (SD) or Tay Sachs disease (TSD).

In an embodiment, the compound is administered orally, subcutaneously, or intravenously.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

Certain embodiments of the disclosure will now be described in greater detail with reference to the attached drawings in which:

FIG. 1 shows the spinal cord of Sandhoff mice exhibit morphological changes within the anterior horn neurons (AHN)s, as well as increased glial fibrillary acidic protein (GFAP) and MAC3 immunoreactivity in an exemplary embodiment of the application. (A-F) Images of spinal cord sections immunostained with normal serum, anti-GFAP, and anti-MAC3 antibodies of hexb$^{+/+}$ wild type and hexb$^{-/-}$ mice. (G-J) Representative immunofluorescent micrographs showing GFAP and GFAP+DAPI in the spinal cords of 60 d hexb$^{+/+}$ and hexb$^{-/-}$ mice. (K-P) Representative immunofluorescent micrographs showing GFAP, NeuN and GFAP+NeuN+DAPI in the spinal cords of 120 d hexb$^{+/+}$ and hexb$^{-/-}$ mice.

FIG. 2 shows a quantitative analysis of neuronal numbers as well as the number of nuclear CHOP and nuclear cleaved caspase 7 positive cells within the anterior horn of cervical, thoracic and lumbar spinal sections from hexb$^{+/+}$ and hexb$^{-/-}$ mice at 60, 80, 100, and 120 d of age in an exemplary embodiment of the application. (A-C) Quantification of NeuN-positive neuronal numbers (D-F) Quantification of nuclear CHOP-positive cells (G-I). Quantification of nuclear cleaved caspase 7-positive cells. *P≤0.05, P<0.0022, *P<0.0002, ****P<0.0001. Error bars, SEM.

FIG. 3 shows representative immunohistological micrographs localizing neuronal specific marker, NeuN, in the spinal cords of hexb$^{+/+}$ and hexb$^{-/-}$ mice in an exemplary embodiment of the application. (A-F) NeuN immunostaining in the cervical region of the spinal cord of hexb$^{+/+}$ and hexb$^{-/-}$ mice. (A-B) A low magnification image of the NeuN immunoreactivity observed within 40 d hexb$^{+/+}$ and hexb$^{-/-}$ mice. Scale bar=100 um. (C-D) High magnification images of anterior horn motor neurons of 40 d hexb$^{+/+}$ and hexb$^{-/-}$ mice respectively. Scale bar=10 μm. (E-F) Low magnification images of NeuN immunoreactivity observed within 120 d hexb$^{+/+}$ and hexb$^{-/-}$ mice, respectively. Scale bar=100 μm.

FIG. 4 shows a quantitative analysis of neuronal morphological changes seen in the spinal cord motor neurons of hexb$^{+/+}$ and hexb$^{-/-}$ mice during the pathogenesis of SD in an exemplary embodiment of the application. (A-B) representative images of a single anterior horn motor neuron from hexb$^{+/+}$ and hexb$^{-/-}$ spinal cords. (C-E) quantification of cell body area, nuclear area, and a ratio of nuclear area over cell body area in hexb$^{+/+}$ and hexb$^{-/-}$ spinal cord sections. Cell Body Area n=9, nuclear area n=7, ratio n=6-7. *P≤0.05, P<0.0022, *P<0.0002, ****P<0.0001. Error bars ±SEM.

FIG. 5 shows representative Western blot analysis for phosphorylated IRE-1, GRP78, ATF6, XBP1, and CHOP protein level in the spinal cord of 120-day-old hexb$^{+/+}$ and hexb$^{-/-}$ mice in an exemplary embodiment of the application. Tubulin was used as a loading control.

FIG. 6 shows representative immunohistological micrographs of ER stress marker, GRP78 (C-D), PDI (E-F), ATF6 (G-H), and XBP1 (I-J) localization within the anterior horn motor neurons of 120-day-old hexb$^{+/+}$ and hexb$^{-/-}$ mouse spinal cords in an exemplary embodiment of the application. Scale bar=10 μm. Normal mouse serum (NS) was used as a negative control (A,B).

Figure 14:
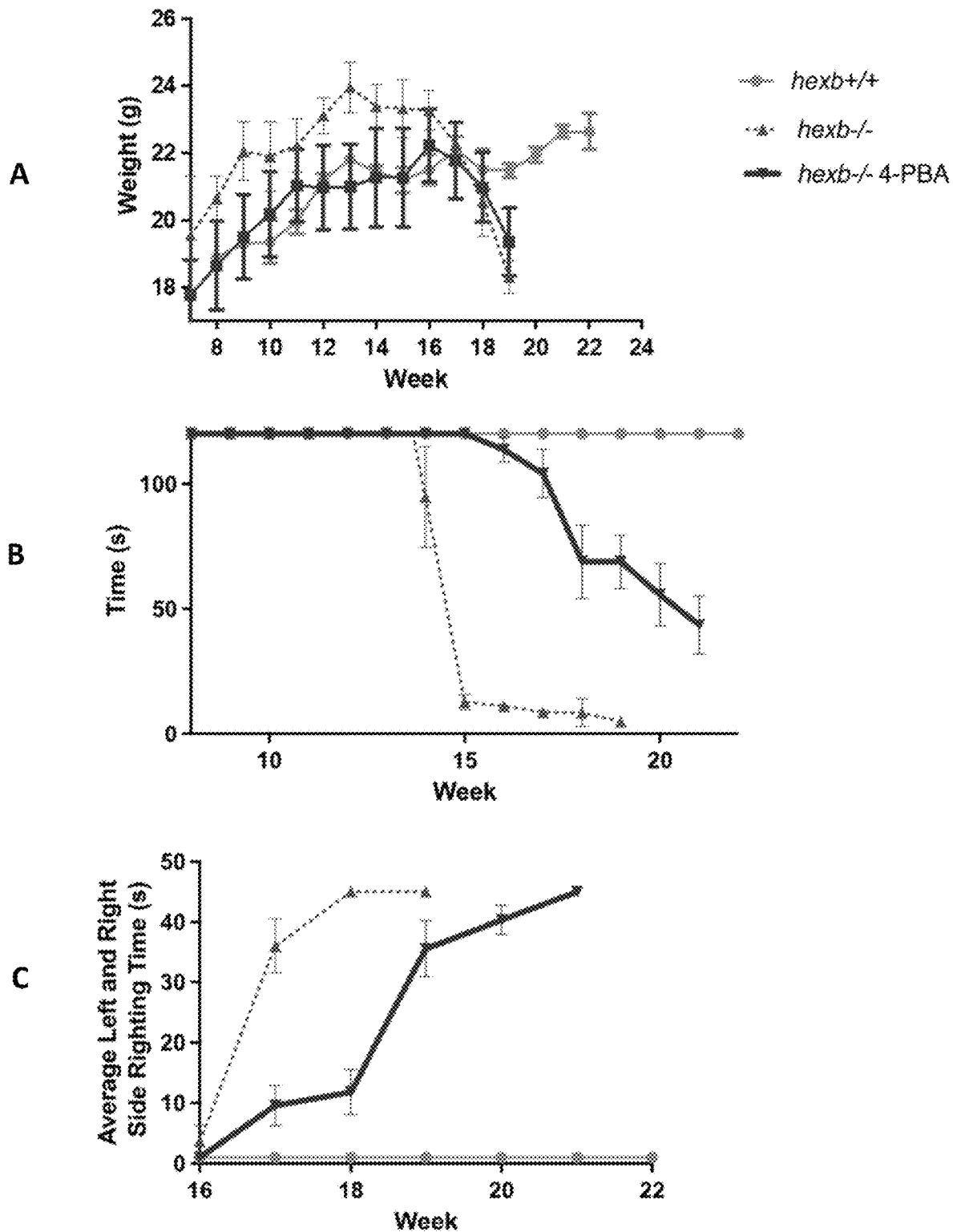
Figure 14:
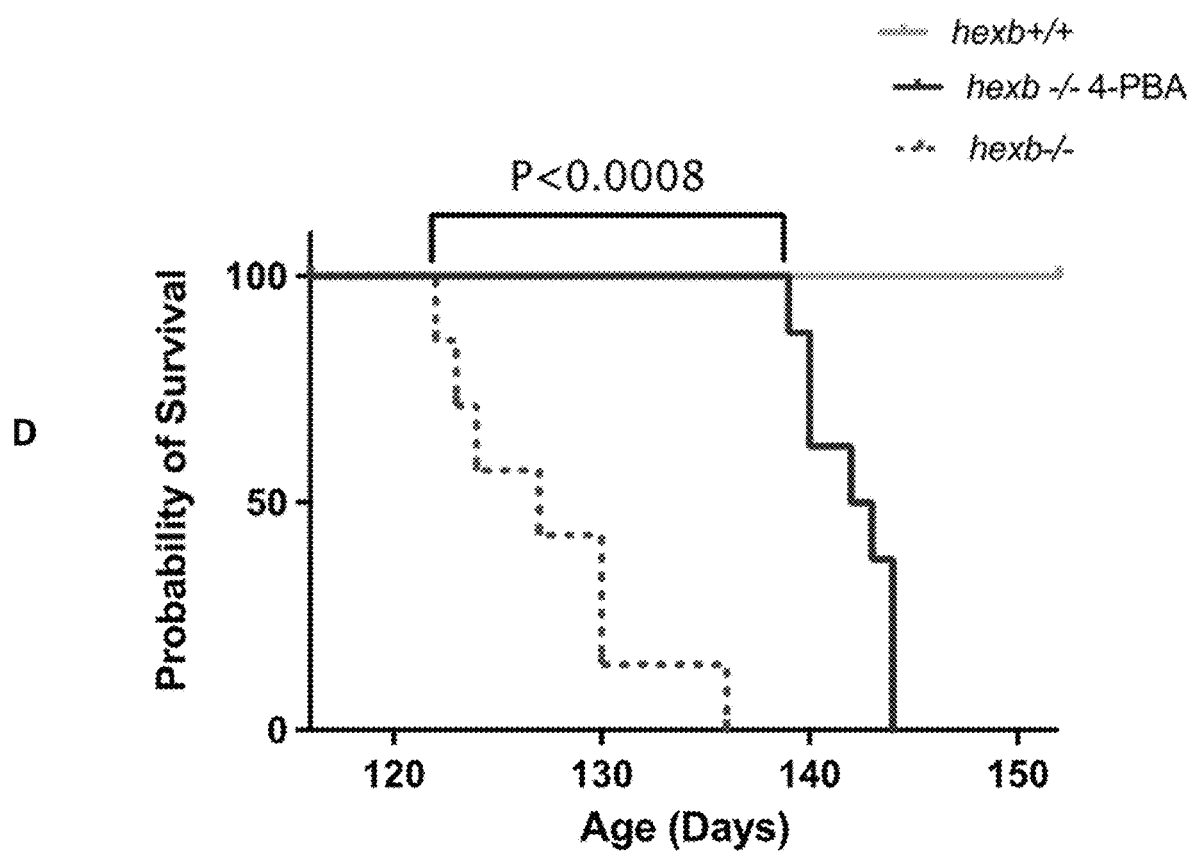

FIG. 14 shows motor neuronal assessment of hexb$^{+/+}$ and hexb$^{-/-}$ mice with and without 4-PBA in an exemplary embodiment of the application. Mice underwent behaviour testing as early as 7 weeks of age, to measure degeneration of various cerebellar and peripheral nervous system functions. Measures of body mass (A), wire hang (B), righting reflex (C), and survivability (D) were recorded every other day. Measurements suggests that 4-PBA has a beneficial effect on Sandhoff disease. Hexb$^{-/-}$ mice administered 4-PBA lived significantly longer than mice without it and displayed significantly faster righting reflex and longer wire hang during later stages of disease, indicating a positive effect on general motor functions. In addition, Hexb$^{-/-}$ mice with 4-PBA have a similar increase in body mass to wildtype mice. Analysis of survival by Mantel-Cox test, P<0.001 between Hexb$^{-/-}$ mice without 4-PBA and Hexb$^{-/-}$ mice with 4-PBA, median survival=127 days and 143 days respectively.

Figure 15:
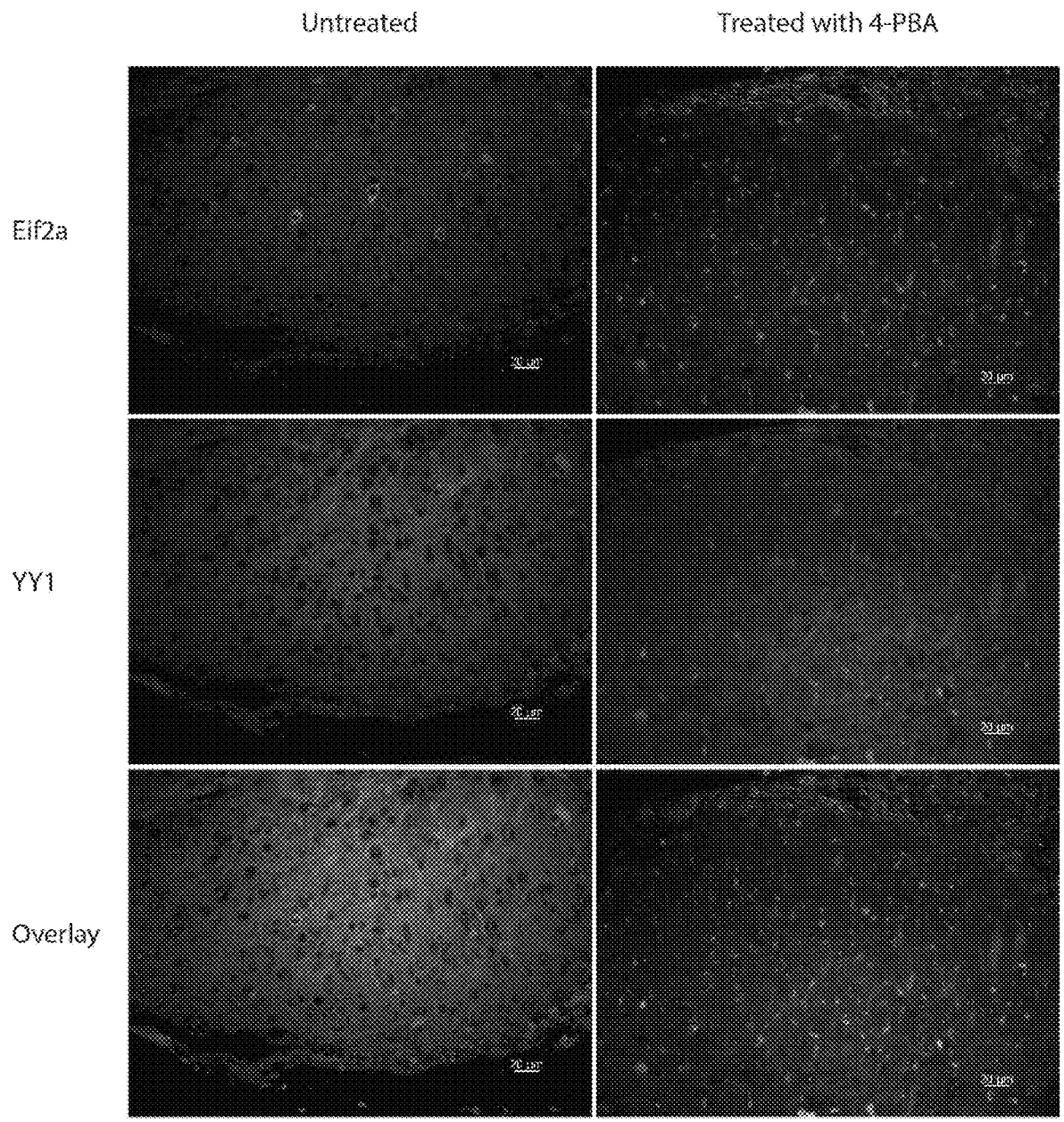

FIG. 15 shows representative immunofluorescent micrographs of phosphorylated eukaryotic factor 2 alpha-positive neurons (p-eIF2α) and the transcription factor YY1 in the spinal cord from Hexb$^{-/-}$ mice untreated or treated with 4-PBA in an exemplary embodiment of the application. The results demonstrated significant reduction in the number of p-eIF2α-positive neurons with cytoplasmic staining after 4-PBA treatment and increase in the nuclear localization of p-eIF2a after 4-PBA treatment. Bars represent 10 μm.

Figure 16:
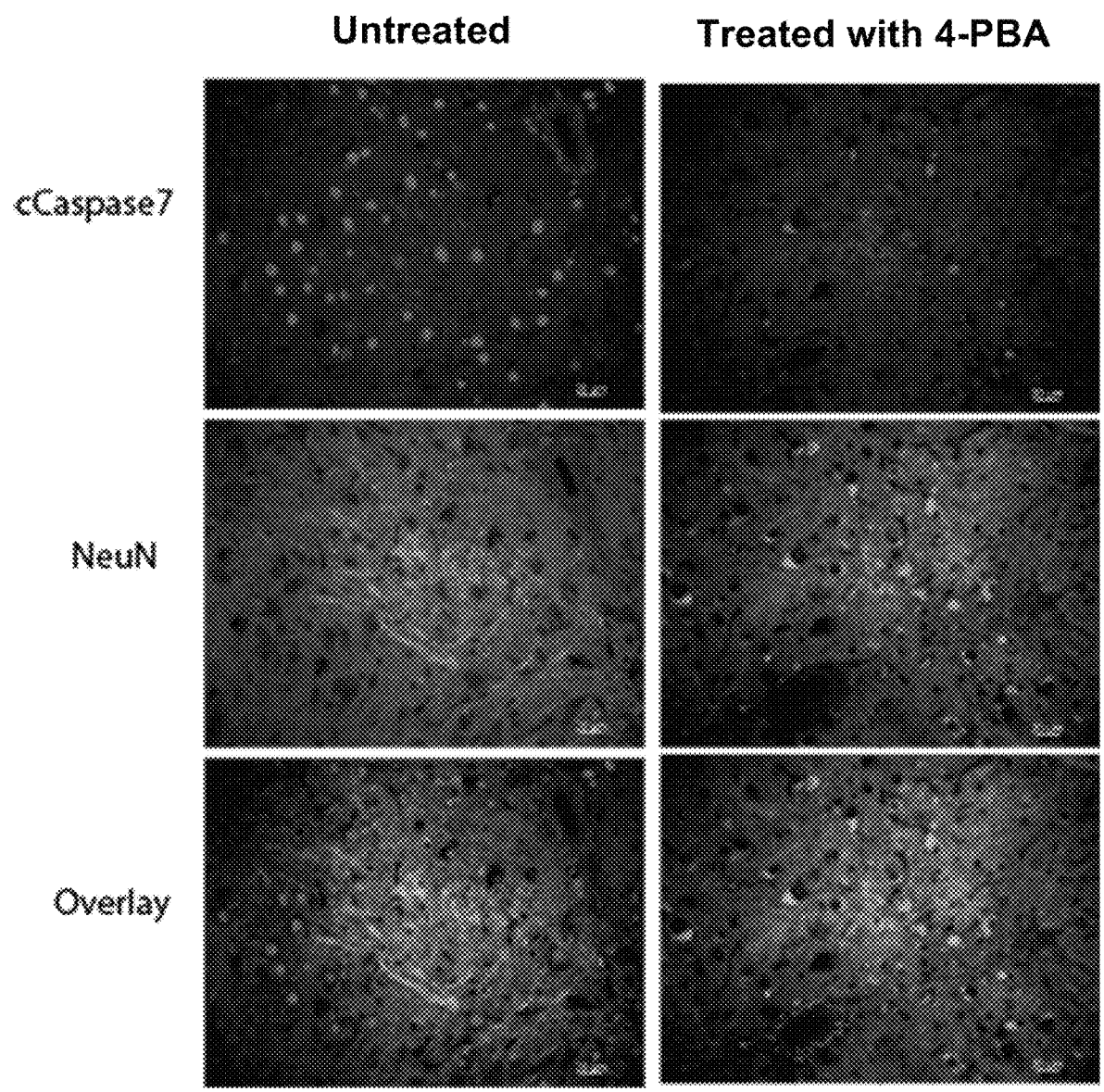

FIG. 16 shows representative immunofluorescent micrographs of cleaved caspase 7-positive neurons and the neuronal marker NeuN in the spinal cord from hexb$^{+/+}$ mice untreated or treated with 4-PBA in an exemplary embodiment of the application. The results demonstrate significant reduction in the number of cCas7 positive cells after 4-PBA treatment. Bars represent 10 μm.

Figure 17:
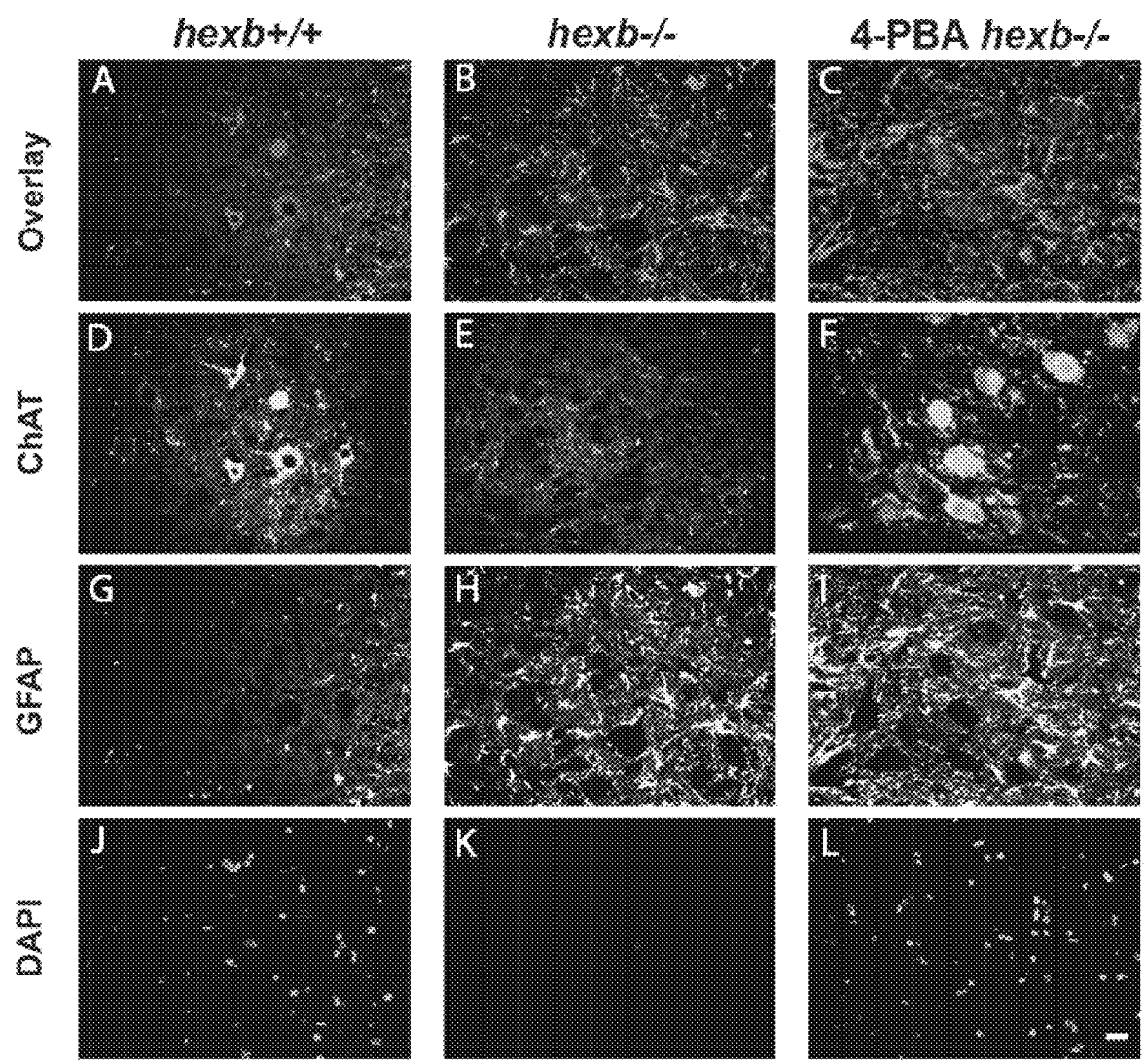

FIG. 17 Shows representative immunofluorescent images of GFAP, ChAT and Dapi staining in the anterior horn of spinal sections from hexb$^{+/+}$, hexb$^{-/-}$ and 4-PBA treated hexb$^{-/-}$ mice. Sections show intense cytosolic ChAT (a marker for cholinergic motor neurons) staining in AHNs of hexb$^{+/+}$ and diminished ChAT staining in hexb$^{-/-}$ with increased GFAP staining (a glial cell marker, indicative of active astrogliosis). In addition, sections show intense cytosolic ChAT staining within viable AHNs with intense GFAP staining in 4-PBA treated hexb$^{-/-}$ AHNs. Bar represents 10 μm.

Figure 18:
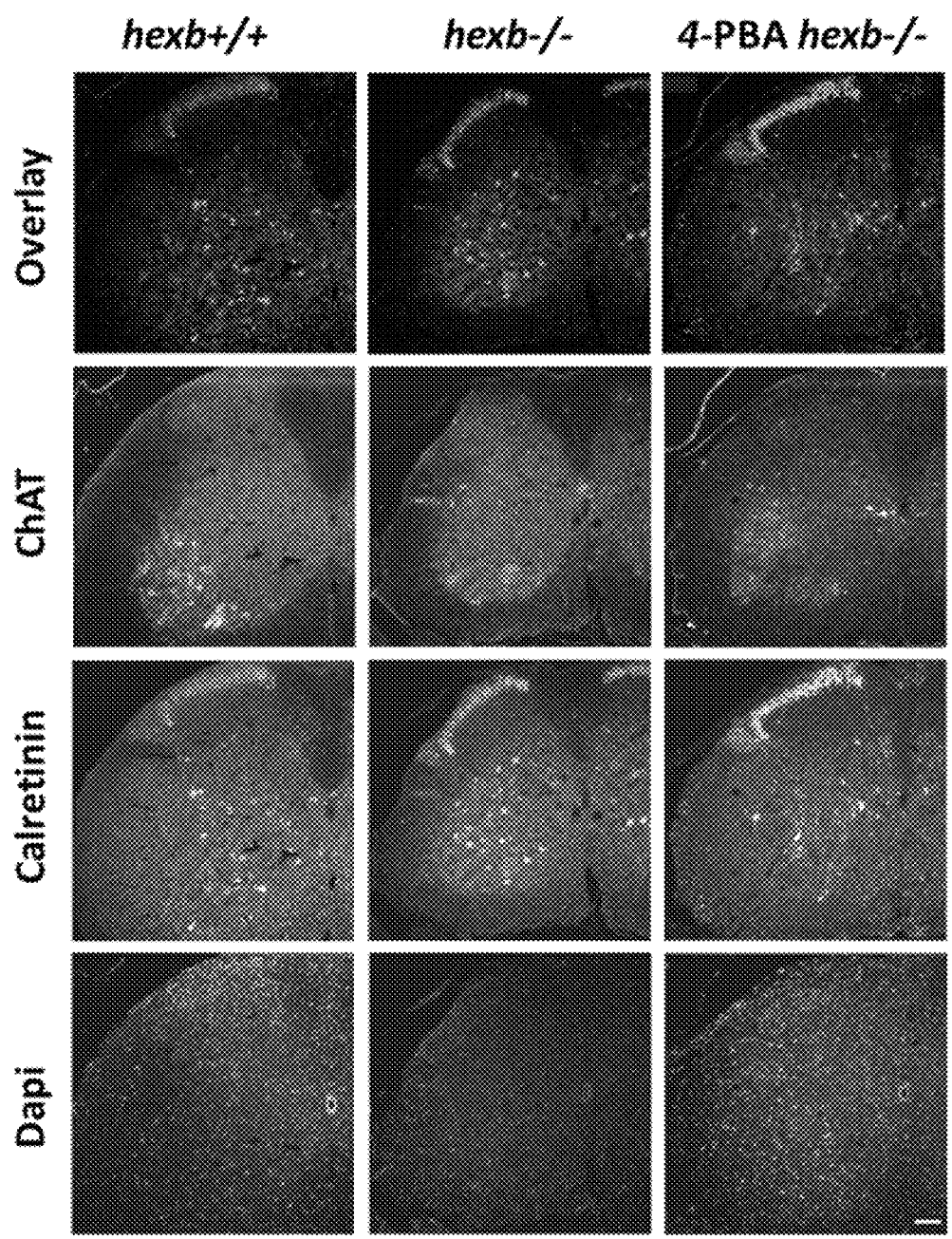

FIG. 18 shows representative immunofluorescent labelling of Calretinin-positive interneurons (sensory), ChAT-positive neurons (motor) and DAPI staining in hexb$^{-/-}$ spinal cord sections in untreated and 4-PBA treated mice. Note that ChAT-positive motor neurons were maintained in anterior horn following 4-PBA treatment, while Calretinin-positive interneurons densely stained posterior horn, with an increase in labeling intensity within the anterior horn of hexb$^{-/-}$ spinal cord mice. Bars represent 10 μm.

Figure 19:
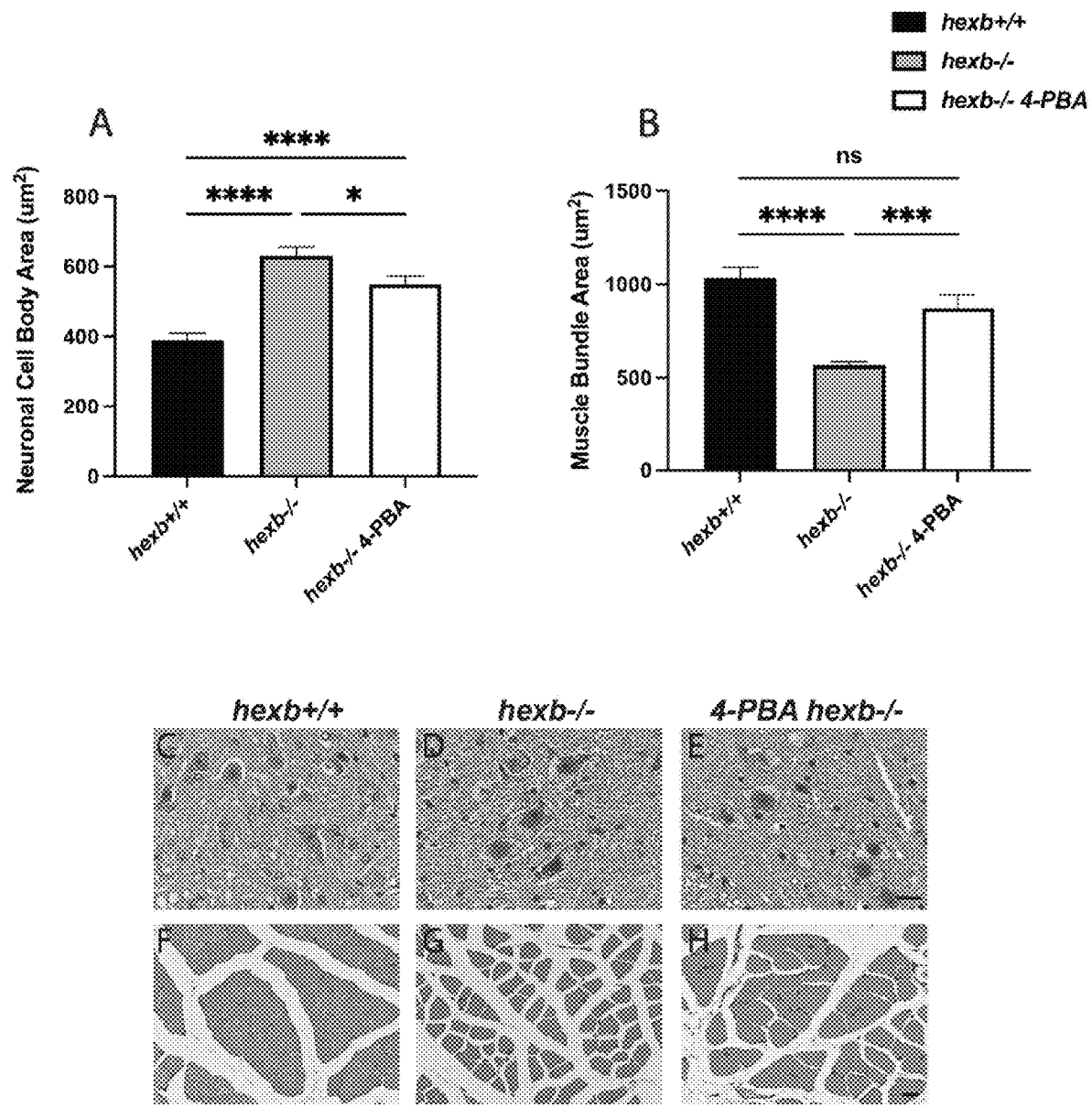

FIG. 19 shows (A) cell body sectional area of the anterior horn neurons and (B) the cross-sectional area of muscle fibers from the muscles surrounding the spinal cord of 80 d hexb$^{+/+}$ and hexb$^{-/-}$ mice. Histological sections of spinal cord (C-E) and skeletal muscle (F-H) from hexb$^{+/+}$, hexb$^{-/-}$, 4-PBA treated hexb$^{-/-}$ mice. Within hexb$^{+/+}$ mice, muscle fibres had an average area of ~1000 um$^2$ while in contrast hexb$^{-/-}$ mice showed a 44% reduction in area with an average of ~570 um$^2$. 4-PBA treatment of hexb$^{-/-}$ maintained normal cross section area of muscle fibers (850 um$^2$), suggesting they received 'normal' functional cholinergic innervation functional cholinergic innervation.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art. It is also to be understood that the terminology used herein is for the purpose of describing particular aspects only and is not intended to be limiting.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies. In addition, all ranges given herein include the end of the ranges and also any intermediate range points, whether explicitly stated or not.

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The abbreviation, "e.g." is derived from the Latin exempli gratia and is used herein to indicate a non-limiting example. Thus, the abbreviation "e.g." is synonymous with the term "for example." The word "or" is intended to include "and" unless the context clearly indicates otherwise.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

The term "solvate" as used herein means a compound, or a salt, co-crystal, polymorph, analog and/or pro-drug of a compound, wherein molecules of a suitable solvent are incorporated in the crystal lattice. A suitable solvent is physiologically tolerable at the dosage administered. When the solvent is water, the solvate is referred to as a "hydrate".

The term "pro-drug" as used herein means a compound, or salt, co-crystal, polymorph, analog and/or solvate of a compound, that, after administration, is converted into an active drug.

The term "subject" as used herein includes all members of the animal kingdom including mammals, and suitably refers to humans. Thus the methods of the present application are applicable to both human therapy and veterinary applications.

The term "subject in need thereof" as used herein refers to a subject having, or is suspected of having, a lysosomal storage disease.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. Treatment methods comprise administering to a subject a therapeutically effective amount of one or more of the compounds of the application and optionally consist of a single administration, or alternatively comprise a series of administrations.

As used herein, the term "effective amount" or "therapeutically effective amount" means an amount of a compound, or one or more compounds, of the application that is effective, at dosages and for periods of time necessary to achieve the desired result.

By "inhibiting, blocking and/or disrupting" it is meant any detectable inhibition, block and/or disruption in the presence of a compound compared to otherwise the same conditions, except for in the absence in the compound.

The term "administered" as used herein means administration of a therapeutically effective amount of a compound, or one or more compounds, or a composition of the application to a cell either in cell culture or in a subject.

The term "therapeutic agent" as used herein refers to any drug or active agent that has a pharmacological effect when administered to a subject.

The term "compound of the application" or "active ingredient" as used herein refers to 4-phenylbutyric acid (4-PBA) or a pharmaceutically acceptable salt, co-crystal, polymorph, solvate, analog and/or pro-drug thereof as described herein. 4-PBA has the following chemical structure:

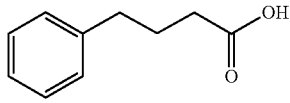 [SMILES: O=C(O)CCCc1ccccc1]

The term "method of the application" as used herein refers to the method of treating a lysosomal storage disease (LSD) as described herein.

It will be understood that any component defined herein as being included may be explicitly excluded by way of proviso or negative limitation, such as any specific compounds or method steps, whether implicitly or explicitly defined herein.

II. Methods of the Application

The present application includes a method of treating a lysosomal storage disease (LSD) comprising administering a therapeutically effective amount of 4-phenylbutyric acid (4-PBA), or a pharmaceutically acceptable salt, co-crystal, polymorph, solvate, analog and/or pro-drug thereof, to a subject in need thereof.

The present application also includes a use of 4-PBA or a pharmaceutically acceptable salt, co-crystal, polymorph, solvate, analog and/or pro-drug thereof for treating a lysosomal storage disease in a subject in need thereof.

The present application also includes a use of 4-PBA or a pharmaceutically acceptable salt, co-crystal, polymorph, solvate, analog and/or pro-drug thereof for the preparation of a medicament for the treatment of a lysosomal storage disease.

4-PBA is a low molecular weight aromatic carboxylic acid. In some embodiments, 4-PBA used in the method of the present application is a pharmaceutically acceptable salt, co-crystal, polymorph, solvate, analog and/or pro-drug of 4-phenylbutyric acid. In some embodiments, 4-PBA is a free acid or a pharmaceutically acceptable salt of 4-PBA. Analogs of 4-PBA include but are not limited to, glycerly(tri-4-PBA), phenyl acetic acid, 2-(4-methoxyphenoxy) acetic acid (2-POAA-OMe), 2-(4-nitrophenoxy) acetic acid (2-POAA-NO2) and 2-(2-naphathyloxy) acetic acid (2-NOAA), as well as pharmaceutically acceptable salts, co-crystals, polymorphs, solvates, and/or pro-drugs thereof. Pharmaceutically acceptable salts, include, for example sodium, potassium, magnesium or calcium salts. The 4-PBA, or a pharmaceutically acceptable salt, co-crystal, polymorph, solvate, analog and/or pro-drug thereof, can be prepared according to methods know in the art or obtained from commercial sources.

Lysosomal storage disease is a metabolic disease caused by defects in lysosomal function and result in lipid accumulation in lysosomes of cells. Examples of LSDs include, but are not limited to Aspartylglucosaminuria, Wolman disease, Cystinosis, Danon disease, Fabry 5 disease, Farber disease, Fucosidosis, Gaucher disease, GM1-Gangliosidoses, GM2-Gangliosidoses, alpha-Mannosidosis, beta-Mannosidosis, Metachromatic leukodystrophy, Sialidosis, Mucolipidosis, Scheie syndrome, Hunter syndrome, Sanfilippo syndrome A, Sanfilippo syndrome B, Sanfilippo syndrome C, Sanfilippo syndrome D, Galactosialidosis, Krabbe disease, Sandhoff disease, Vogt-Spielmeyer disease, Hurler syndrome, Niemann-Pick disease, I-cell disease (mucolipidosis II), pseudo-Hurler polydystrophy, Morquio syndrome, Maroteaux-Lamy syndrome, Sly syndrome, Mucopolysaccharidosis type IX, Multiple sulfatase deficiency, Batten disease, Tay-Sachs disease, Pompe disease, Batten disease, Batten disease, late infantile, Northern Epilepsy, Pycnodysostosis, Schindler disease, Sialuria, and Salla disease.

In some embodiments, the lysosomal disease is GM2 gangliosidoses. In the GM2 gangliosidosis, substrate accumulation occurs within lysosomes of neurons throughout the CNS, particularly the spinal cord. In some embodiments, the GM2 gangliosidoses is selected from Tay Sachs disease (TSD) and Sandhoff disease (SD). In some embodiments, the GM2 gangliosidoses disease is TSD. In some embodiments, the GM2 gangliosidoses disease is SD. These diseases can present with a multiplicity of symptoms including cognitive and speech impairments, ataxia, and lower motor neuron disease.

The SD disease is classified according to disease severity as 1) infantile, 2) juvenile, or 3) late-onset forms. As such, in some embodiments, the SD is selected from infantile, juvenile, and late-onset forms. In some embodiments, the SD is a late-onset form.

In some embodiments, the methods and uses of the present application achieve at least one of delayed neurological symptoms, reduced pain, improved motor neuromuscular function or increase life span. In some embodiments, motor functions include but are not limited to, improvement in balance, motor coordination, gait disturbances, muscle weakness, muscle atrophy, fasciculations, and/or tremors.

In some embodiments, the methods and uses of the present application reduce pain.

In some embodiments, the methods and uses of the present application achieve increased lifespan.

The ER stress response consists of multiple pathways that work together to initiate a variety of downstream cellular events that will either act to protect the cell, i.e., pro-survival, or in the case of severe and prolonged ER stress will result in the triggering of apoptotic events. Examples of ER stress markers include but are not limited to glial fibrillary acidic protein (GFAP), activating transcription factor 6 (ATF6), XBP1 (X-Box binding protein 1), glucose regulatory protein 78 (Grp78), IRE1-phos, homologous protein (CHOP), protein disulfide isomerase (PDI), caspase 7, poly (ADP-ribose) polymerase (PARP) and C/EBP.

The unfolded protein response (UPR) pathway is a signal transduction cascade which serves as a regulator of cellular homeostasis. UPR pathway can be mediated by various markers know in the art, such as CHOP (a pro-apoptotic transcription factor), apoptotic markers such as cleaved PARP or cleaved caspase 7, and other markers known in the art.

It has been shown in the present application that in LSD, physiological conditions that cause endoplasmic reticulum (ER) stress activate the unfolded protein response (UPR) and lead to apoptosis of neurons. It has been further shown in the present application, that 4-PBA inhibits a target within neurodegeneration mediated unfolded protein response (UPR) pathway in lower motor neurons.

As such, in some embodiments, the methods and uses of the present application comprise inhibiting a target within neurodegeneration mediated unfolded protein response (UPR) pathway in lower motor neurons.

Lower motor neurons are located in the brainstem and the spinal cord and send fibers out to muscles. When a lower motor neuron degenerates, the muscle fibers it normally activates become disconnected and do not contract, causing muscle weakness and diminished reflexes. Loss of neurons results in weakness, muscle atrophy (wasting) and painless weakness are the clinical hallmarks of motor neuron disease. In some embodiments, the lower motor neurons are located in the anterior horn.

In some embodiments, the target that is modulated by a compound of the application, for example, 4-PBA or a pharmaceutically acceptable salt thereof, is one or more of the following: glial fibrillary acidic protein (GFAP), activating transcription factor 6 (ATF6), XBP1 (X-Box binding protein 1), glucose regulatory protein 78 (Grp78), IRE1-phos, homologous protein (CHOP), protein disulfide isomerase (PDI), caspase 7, poly (ADP-ribose) polymerase (PARP) and C/EBP.

In some embodiments, the methods and uses of the present application comprise reduction in the number of cytosolic p-eIF2α-positive neurons in a spinal cord of the subject. As such, a compound of the application, for example, 4-PBA or a pharmaceutically acceptable salt thereof, alleviates ER stress.

In some embodiments, the methods and uses of the present application comprise reduction in the number of cCas7 positive neurons in a spinal cord of the subject. As such, a compound of the application, for example, 4-PBA or a pharmaceutically acceptable salt thereof, reduces neurodegeneration.

In some embodiments, the methods and uses of the present application comprise maintaining the activity of the enzyme choline acetyltransferase (ChAT). In some embodiments, the methods and uses of the present application comprise, reduction in calretinin-positive interneurons. As such, a compound of the application, for example, 4-PBA or a pharmaceutically acceptable salt thereof, maintains cholinergic motor neurons.

In some embodiments, the methods and uses of the present application comprise maintaining muscle myofibril integrity. As such, a compound of the application, for example 4-PBA or a pharmaceutically acceptable salt thereof, maintains neuromuscular innervation and reduces muscle atrophy.

In some embodiments, the subject is a mammal. In some embodiments, the subject is human.

Treatment methods of the present application comprise administering to a subject a therapeutically effective amount of a compound of the application and optionally consist of a single administration, or alternatively comprise a series of administrations, and optionally comprise concurrent administration or use of one or more other therapeutic agents. For example, in some embodiments, the compound of the application is administered at least once a week. In some embodiments, the compound of the application is administered to the subject from about one time per two or three weeks, or about one time per week to about once daily for a given treatment. In another embodiment, the compound of the application is administered 2, 3, 4, 5 or 6 times daily. The length of the treatment period depends on a variety of factors, such as the severity of the disease, disorder or condition, the age of the subject, the concentration and/or the activity of the compound of the application, and/or a combination thereof. It will also be appreciated that the effective dosage of the compound of the application used for the treatment may increase or decrease over the course of a particular treatment regime. Changes in dosage may result and become apparent by standard diagnostic assays known in the art. In some instances, chronic administration may be required. For example, the compound of the application is administered to the subject in an amount and for duration sufficient to treat the subject.

The compound of the application can be administered by any appropriate administration route, for example, orally, parenterally, intravenously, intradermally, intramuscularly, subcutaneously, sublingually, transdermally, bronchially, pharyngolaryngeal, intranasally, topically such as by a cream or ointment, rectally, intraarticular, intracisternally, intrathecally, intravaginally, intraperitoneally, intraocularly, by inhalation, bucally or as an oral or nasal spray. The route of administration may vary, however, depending upon the condition and the severity of the disease.

In some embodiments, the compound of the application is administered orally. In some embodiments, the compound of the application is administered parenterally. In some embodiments, the compound of the application is administered intravenously.

The compound of the application can be administered in any of the known dosage forms standard in the art, including without limitation, solid dosage form, semi-solid dosage form, or liquid dosage form, as well as subcategories of each of these forms.

In some embodiments, the compound of the application is administered in a liquid dosage form. In some embodiments, the compound of the application is administered in a solid dosage form.

Solid dosage forms for oral administration include capsules, caplets, tablets, pills, powders, lozenges, and granules. As used herein, the term "tablet" is intended to include compressed tablets, coated tablets, matrix tablets, osmotic tablets, and other forms known in the art, as more fully described above. As used herein, the term "capsule" is intended to include capsules in which the body of the capsule disintegrates after ingestion to release particulate contents which exhibit the desired sustained-release behavior, and also capsules for which the body of the capsule remains substantially intact during its residence in the GI tract. Multiparticulate dosage forms are also contemplated, wherein dosage form contains a multiplicity of particles whose totality represents the intended therapeutically useful dose of the compound of the application.

In such solid dosage forms, the compound of the application is mixed with at least one inert, pharmaceutically acceptable excipient or carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions for rectal or vaginal administration are suitably suppositories which can be prepared by mixing the compound of the application with suitable non-irritating excipients or carriers such as cocoa butter, polyethylene glycol or a suppository wax which are solid at ambient temperature but liquid at body temperature and therefore melt in the rectum or vaginal cavity and release the active compound.

Semi-liquid dosage forms include those dosage forms that are too soft in structure to qualify for solids, but too thick to be counted as liquids. These include creams, pastes, ointments, gels, lotions, and other semisolid emulsions containing the active compound of the present application.

The ointments, pastes, creams and gels may contain, in addition to a compound of the application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Liquid dosage forms for oral administration include pharmaceutically acceptable emulsions, microemulsions, solutions, suspensions, syrups and elixirs. In addition to the compound of the application, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In some embodiments, the compound of the application can be dissolved in water, juice or milk.

Dosage forms for topical or transdermal administration of a compound of the application include ointments, pastes, creams, lotions, gels, powders, solutions, sprays, inhalants or patches, optionally mixed with degradable or nondegradable polymers. The compound of the application is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

Formulations containing a compound of the application may be administered through the skin by an appliance such as a transdermal patch. Patches can be made of a matrix such as polyacrylamide, polysiloxanes, or both and a semi-permeable membrane made from a suitable polymer to control the rate at which the material is delivered to the skin. Other suitable transdermal patch formulations and configurations are described in U.S. Pat. Nos. 5,296,222 and 5,271,940, as well as in Satas, D., et al, "Handbook of Pressure Sensitive Adhesive Technology, 2nd Ed.", Van Nostrand Reinhold, 1989: Chapter 25, pp. 627-642.

Powders and sprays can contain, in addition to a compound of the application, excipients such as lactose, talc, silicic acid, aluminum hydroxide, calcium silicates and polyamide powder, or mixtures of these substances. Sprays can additionally contain customary propellants such as chlorofluorohydrocarbons.

The formulations may be prepared by any of the methods well known in the art of pharmacy. All methods include the step of bringing into association a compound of the application with the carrier which constitutes one or more accessory ingredients. In general, the formulations are prepared by uniformly and intimately bringing into association the compound of the application with liquid carriers or finely divided solid carriers or both and then, if necessary, shaping the product into the desired formulation.

The dosage of the compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. A compound of the application may be administered initially in a suitable dosage that may be adjusted as required, depending on the clinical response. Dosages will generally be selected to maintain a serum level of a compound of the application from about 0.01 µg/cc to about 1000 µg/cc, or about 0.1 µg/cc to about 100 µg/cc. As a representative example, oral dosages of a compound of the application will range between about 0.01 mg per day to about 1000 mg per day for an adult, suitably about 0.1 mg per day to about 500 mg per day, more suitably about 1 mg per day to about 200 mg per day.

For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg of a compound of the application is administered.

For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg of a compound of the application.

In some embodiments, the compound of the application is administered from about 0.1 g/kg body weight/day to about 10 g/kg body weight/day, about 0.2 g/kg body weight/day to about 8 g/kg body weight/day, about 0.5 g/kg body weight/day to about 6 g/kg body weight/day, about 1 g/kg body weight/day to about 5 g/kg body weight/day, about 2 g/kg body weight/day to about 4 g/kg body weight/day and amounts therebetween. In some embodiments, the compound of the application is administered at about 0.5 g/kg body weight/day.

For administration in suppository form, a representative amount is from about 0.1 mg/kg to about 10 mg/kg or about 0.1 mg/kg to about 1 mg/kg of a compound of the application. A compound of the application may be administered in a single daily, weekly or monthly dose or the total daily dose may be divided into two, three or four daily doses.

In some embodiments, therapeutically effective amounts of a compound of the application are achieved by administering single or multiple doses during the course of an imaging and/or treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

In some embodiments, effective amounts vary according to factors such as the disease state, age, sex and/or weight of the subject. In a further embodiment, the amount of a given compound of the application that will correspond to an effective amount will vary depending upon factors, such as the given compound(s), the pharmaceutical formulation, the route of administration, the type of condition, disease or disorder, the identity of the subject being treated, and the like, but can nevertheless be routinely determined by one skilled in the art.

In some embodiments, the method of the present application comprising administering a compound of the application in combination with a second compound of the application and/or another therapeutic agent or any other treatments for lysosomal storage diseases known in the art.

EXAMPLES

The following non-limiting examples are illustrative of the present disclosure:

Methods and Materials

Mice

Mouse work was conducted under the animal utilization protocol (AUP) in accordance with the Ontario Animals for Research Act specifications and the Animal Research Ethics Board (AREB) guidelines. The Sandhoff model mice (hexb$^{-/-}$ on a C57BL/6 background) were generously donated by Dr. R. Gravel (University of Calgary, Canada) and have been previously characterized [14].

Genotyping

Mice were genotyped using isolated tail genomic DNA as a template for polymerase chain reaction. For Hexb genotyping, 2 forward primers were used for wild type 5'-GGTTTCTACAAGAGACATCATGGC-3' [SEQ ID NO:1] and knock out 5'-GATATTGCTGAAGAGCTTGGCGGC-3' [SEQ ID NO:2], with a reverse primer 5'-CA ATCGGTGCTTACAGGTTTCATC-3' [SEQ ID NO:3] to generate a 141 bp product for the wild-type allele and a 700 bp product for the knockout allele. The thermocycler program consisted of 35 cycles of 94° C. for 30 s, 60° C. for 30 s and 72° C. for 45 s.

Animal Protocols

Protocol one: Two groups of hexb$^{-/-}$ mice (n=10 per group); One group was administered 4-PBA (Scandinavian Formulas, Inc.) 4 mg/ml (0.4% w/v) in drinking water at 40 d of age. Body weights and vitals were monitored, and motor neuromuscular function were assessed every other day starting at 50 d of age until end point.

Protocol Two: Two groups of hexb$^{-/-}$ mice at 40 d of age (n=4 per group) were set. One group was administered 4-PBA 4 mg/ml (0.4% w/v) in drinking water and one group did not receive any 4-PBA. Mice were perfused at 80 d, with formalin and processed for immunocytochemistry. Spine sections from treated and untreated mice were immunolabelled with multiple antibodies and evaluated.

Immunocytochemistry

Hexb$^{+/+}$ and hexb$^{-/-}$ mice were harvested at a range of ages including 40, 60, 80, 100, and 120 d. They were perfused with 1× phosphate-buffered saline (PBS) and fixed with 10% buffered formalin. The spinal cord was harvested, sectioned into the three main regions (cervical, thoracic, and lumbar), and were then embedded in paraffin wax. Four-micrometer thick cross-sections of the spinal cord were cut and mounted on charged slides. Immunocytochemistry was then performed on these samples using Vectastain Elite ABC Universal Plus Kit (Vector Laboratories: PK-8200). Slides were rehydrated, first by washing slides with xylene then by washing them with a 1:1 solution of xylene and ethanol (EtOH) followed by washes in 100% EtOH, 95% EtOH, 70% EtOH, 70% EtOH/1% hydrogen peroxide solution (to quench endogenous peroxidase), 70% EtOH/1% lithium carbonate solution, 70% EtOH, and finally, 50% EtOH. Next, antigen retrieval in a sodium citrate buffer (pH 6) was performed by microwaving the slides at 1 min intervals until boiling and then maintaining a boil for 5 minutes. The slides were then washed with tap water followed by a wash in glycine. Following, the slides were then incubated with bloxall blocking solution for 10 minutes, followed by a 5 minute wash with PBS. Slides were then blocked with 2.5% horse serum for 20 minutes. Primary antibodies for ER stress markers including anti-GRP78 (1:200, novus biologicals: NBP1-06277), anti-ATF6 (1:50, novus biologicals: NBP1-40256), anti-XBP1 (1:100, novus biologicals: NBP1-77681), anti-PDI (1:200, cell signaling), anti-CHOP (1:400, novus biologicals: NBP2-13172), anti-cleaved PARP (1:400, novus biologicals; NB100-56599), anti-PARP (1:400, cell signaling; 9542), anti-cleaved caspase 7 (1:400, cell signaling; 8438S), anti-NeuN (1:200, novus biologicals; NBP1-92693) and normal mouse serum (1:500, Santa Cruz Biotech; sc-2025) were used. Slides were incubated with antibodies overnight at 4° C. Slides were washed with 1×PBS+0.05% TWEEN20 for 3×5 minutes, prior to application of the secondary antibody. Slides were then incubated with prediluted biotinylated horse anti-mouse/anti-rabbit IgG secondary antibody for 30 minutes. Slides were then again washed with 1×PBS+0.05% TWEEN20 and Vectastain elite ABC reagent was then add to the slides for 30 minutes and then washed with 1×PBS. Equal amounts of ABC reagent 1 and 2 were mixed and slides were incubated with the solution until staining appeared (about 5-20 minutes) and then were rinsed with tap water. Counterstaining was then completed by placing slides into 0.1% methylene blue for 1.5 minutes and removing excess with water. Slides were then washed in EtOH starting at 50% and going up to 100%, then 1:1 xylene to EtOH, and finally 100% xylene. Lastly, glass slide covers were mounted using Permount histological mounting medium (Fisher Scientific: SP15-500). Images were captured at various magnifications via a Nikon Eclipse Ci microscope, equipped with a Nikon DS-Ri2 camera (Dr. Austin's Lab, St. Josephs Health Care, Hamilton).

Western Blot

Mice were anesthetized with 7.5% avertin and were perfused with PBS through the left ventricle of the heart. The spinal cord was harvested and divided into the three main regions (cervical, thoracic, and lumbar), and snap frozen in liquid nitrogen. Lysis buffer containing ethylenediaminetetraacetic acid (EDTA) (ThermoFisher; 78440) and protease inhibitor (ThermoFisher; 78440) that were diluted with RIPA buffer (ThermoFisher; 89900) was added to the samples which were then sonicated and homogenized. Homogenized samples were then aliquoted and Laemmli sample buffer (4×) was added to the lysate before being boiled for 10 minutes at 100° C. Samples were then loaded into an 10% SDS-PAGE resolving gel with a 5% stacking gel in equal protein quantity as determined by protein assay. SDS-PAGE was run at 90V for 120 min. Run gels were then transferred at 4° C. for 60 min at 100V onto a nitrocellulose membrane. Membranes were then blocked for 60 min using 5% nonfat powdered milk in tris-buffered saline with Tween-20 (TBST) (10 mM Tris-HCl, 150 mM NaCl, 0.05% Tween-20) on a rotator at 4° C. Membranes were then incubated with a primary antibody, anti-GRP78 (novus biologicals: NBP1-06277, 1:1000; Anti-Rabbit), anti-ATF6

(novus biologicals:NBP1-40256, 1:1000; Anti-Mouse), anti-XBP1 (novus biologicals, 1:1000; Anti-Rabbit), anti-IRE1-phos (novus biologicals: NB100-2323, 1:1000; Anti-Rabbit), and anti-CHOP (novus biologicals: NBP2-13172, 1:1000; Anti-Rabbit) and were left overnight on a rotator at 4° C. Blots were then washed with 1×TBST for 3×5 min. Next, the correct horseradish peroxidase conjugated secondary antibody was added to the membrane, with a dilution of 1:2000, for 60 minutes at room temperature followed by 3 washes in 1×TBST. Blotted membranes were then incubated with Amersham ECL western blotting detection reagent (Cytiva: RPN2106) for 1 minute before being exposed to Amersham Hyperfilm ECL high performance chemiluminescence film (GE Healthcare: 28906836) for varying lengths of time dependent on the antibody. The X-ray films of blots were scanned and saved as TIFF files.

Immunofluorescence

Spinal cords from $hexb^{+/+}$ and $hexb^{-/-}$ mice were harvested at 40, 60, 80, 100, and 120 d and embedded in paraffin as described above. Samples were rehydrated, first by washing slides with xylene then by washing them with a 1:1 solution of xylene and ethanol (EtOH) followed by washes in 100% EtOH, 95% EtOH, 70% EtOH, 70% EtOH/1% lithium carbonate solution, 70% EtOH, and finally, 50% EtOH. Next, antigen retrieval in a sodium citrate buffer (pH 6) was performed by microwaving the slides at 1 min intervals until boiling and then maintaining a boil for 5 minutes. The slides were then washed with tap water followed by a wash in glycine. Following, the slides were then incubated with bloxall blocking solution for 10 minutes, followed by a 5 minute wash with PBS. Slides were then blocked with 2.5% horse serum for 20 minutes. Samples were then double labelled with a combination of anti-GFAP (1:100, Sigma; G9269), anti-ChAT (1:200, SIGMA), anti-Calretinin (1:200, Proteintech) and anti-NeuN (1:100, novus biologicals; N.BP1-92693). Slides were incubated with antibodies overnight at 4° C. Samples were washed with 1×PBS+0.05% TWEEN20 for 3×5 minutes, prior to application of the secondary antibody. Following, slides were double labeled with appropriate Alexa Fluor secondaries (Invitrogen, goat anti-rabbit 488: A11037, goat anti-mouse 594: A11029) and then again washed with 1×PBS+0.05% TWEEN20. Finally, the slides were mounted with ProLong Diamond antifade mountant reagent with DAPI (Invitrogen: P36966). Samples were imaged using Ziess Axiovert 200 scope equipped with an HBO 100 mercury lamp.

Statistical Software

For data sets with groups of two that needed to be compared, t-tests were used to test for differences between means at $P<0.05$. Data sets of three or more groups were tested for differences between means at $P<0.05$ using one-way ANOVA. This was followed by Tukey's post hoc test for all data sets with equal variance and high normality between groups. For sample sets with unequal sample sizes or variance, Kruskal-Wallis test was used for a pairwise comparison. All statistical analyses were performed using GraphPad Prism 9 (V.9.3.0).

Results

Targeted disruption of the hexb gene resulted in a mouse model of Sandhoff disease with a wide range of behavioural, histological, and morphological abnormalities corresponding well to the manifestation of Sandhoff disease and Tay Sachs disease in humans. Histologically, spinal motor neurons, specifically anterior horn neurons (AHNs), show significant differences in their morphology and structural integrity between $hexb^{+/+}$ and $hexb^{-/-}$ mice. In $hexb^{+/+}$ mice, AHNs show a fusiform, conical, or star-like shape with a smooth cell membrane and fine organelle structures, i.e., Nissl bodies within the cytoplasm. The nucleus and nuclear membrane are spherical and smooth (FIG. 1A). In contrast, anterior horn neurons in $hexb^{-/-}$ mice at end point (120 d) show an engorged and rounded shape due to the significant amount of lipid accumulation within the lysosomes. Their cell membrane is displaced due to swollen lysosomes, and organelle structures are no longer visible. Additionally, the nuclei are shrunken and have a star shaped halo surrounding the nuclear membrane, the size of which is dependent on the extent of accumulation (FIG. 1D).

Figure 2:
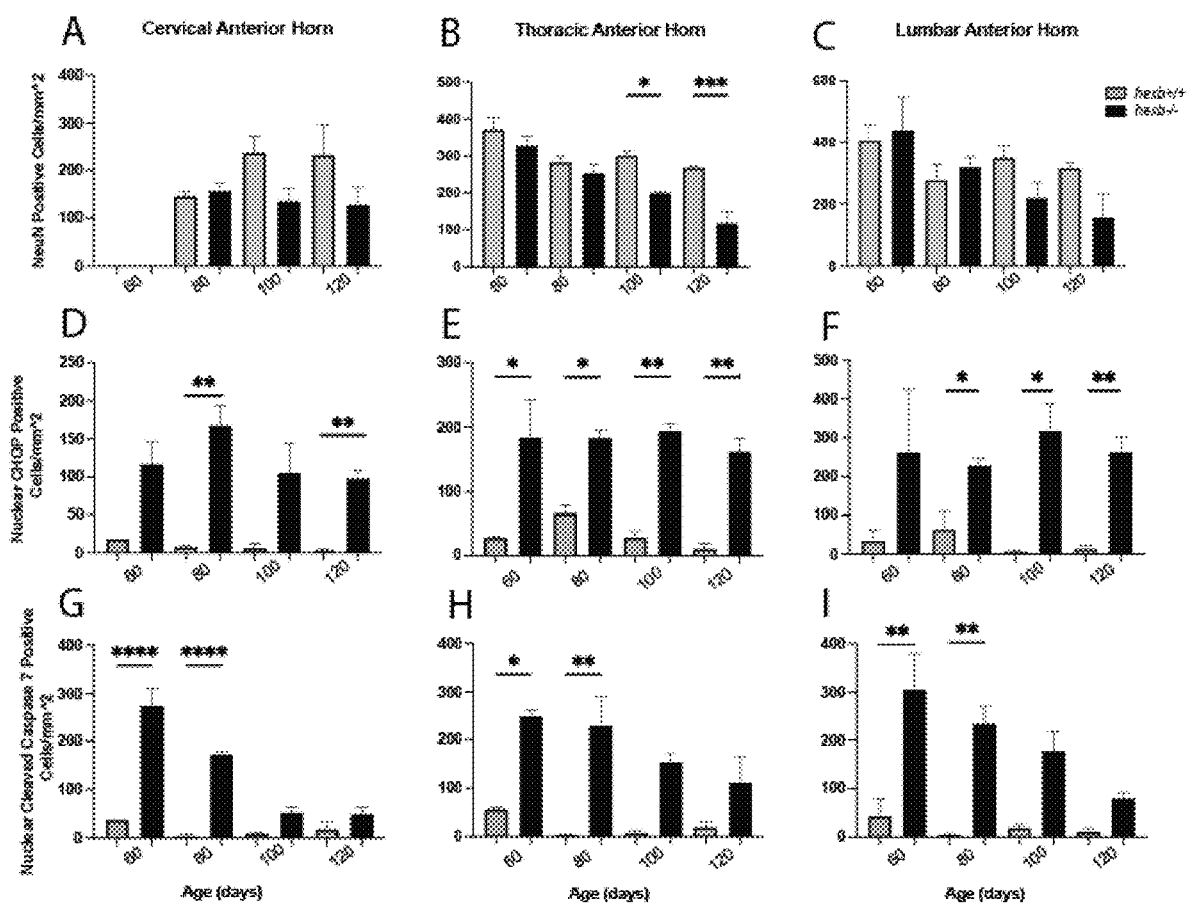
Figure 3:
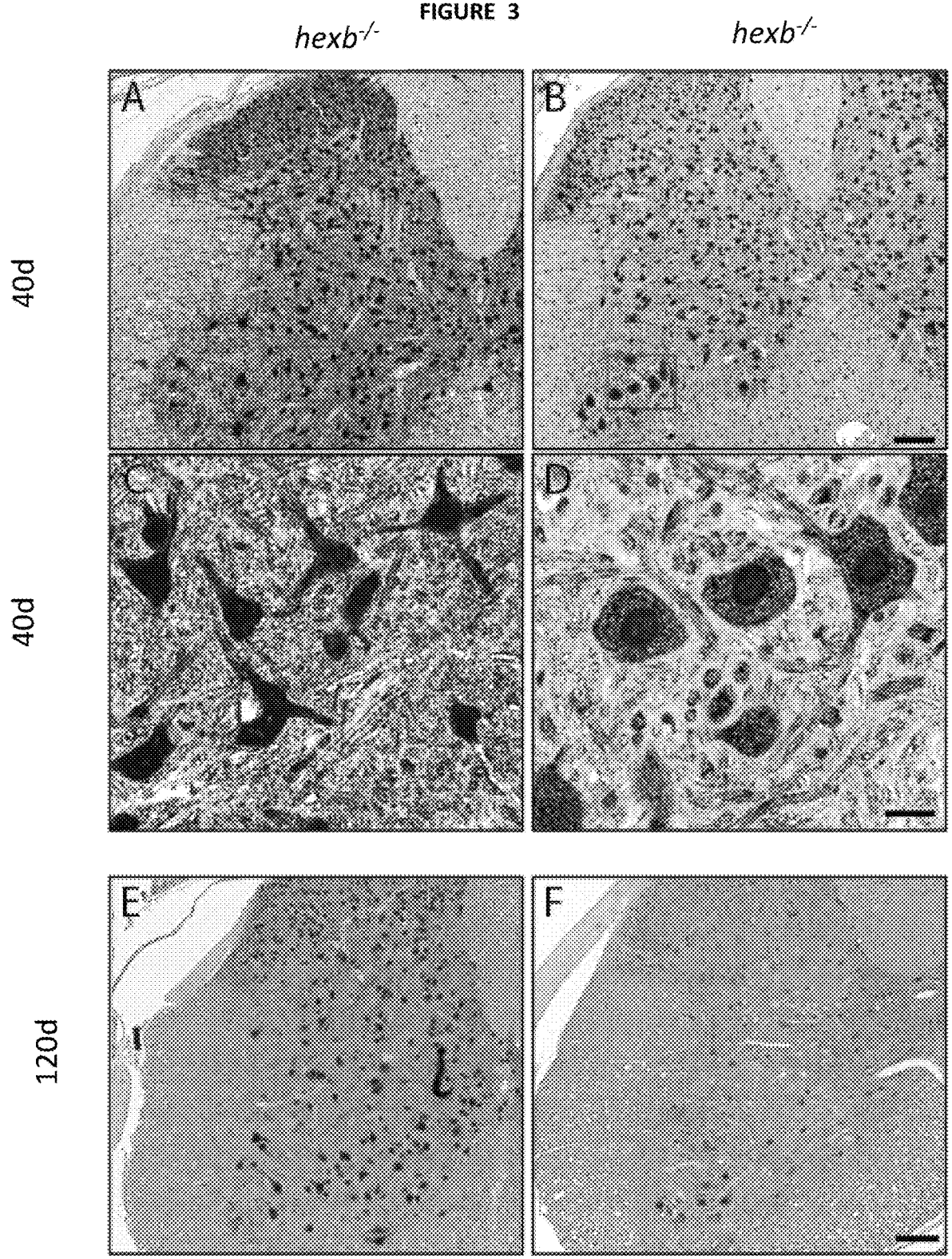

Additionally, the degree of neuronal loss within the anterior horn was assessed temporally using a nuclear neuronal marker, NeuN (FIG. 2 A-C). The number of NeuN positive cells within a defined region of the anterior horn were counted. Three independent sets of spinal cords were evaluated, and the numbers were standardized as cells/mm². At 60 d, spinal cord samples across all three regions showed comparable anterior horn neuronal numbers between $hexb^{+/+}$ and $hexb^{-/-}$ mice. A similar trend was seen at 80 d and again was consistent throughout the three spinal cord regions. Later in disease progression, beginning at 100 days, a deterioration of neuronal numbers was observed in $hexb^{-/-}$ spinal cords in comparison to $hexb^{+/+}$ mice. By 120 d, severe neuronal loss was noted with about 45% decrease in the cervical section, about 56% within the thoracic segment, and about 50% in the lumbar region. By the terminal stages of the disease an average of 50% of anterior horn neurons throughout the entire spinal cord have died, which predictably resulted in a detrimental outcome (FIG. 3 D,E). These data support the notion that this specific population of spinal cord neurons is a major target for the disease and the loss of these neurons correlates with its clinical manifestation. Accompanying this mass neuronal loss and these intracellular variations, diseased neurons also appeared to have retracted and lost axonal projections starting as early as 40 d when compared to $hexb^{+/+}$ neurons. (FIG. 3 A-D).

Figure 1:
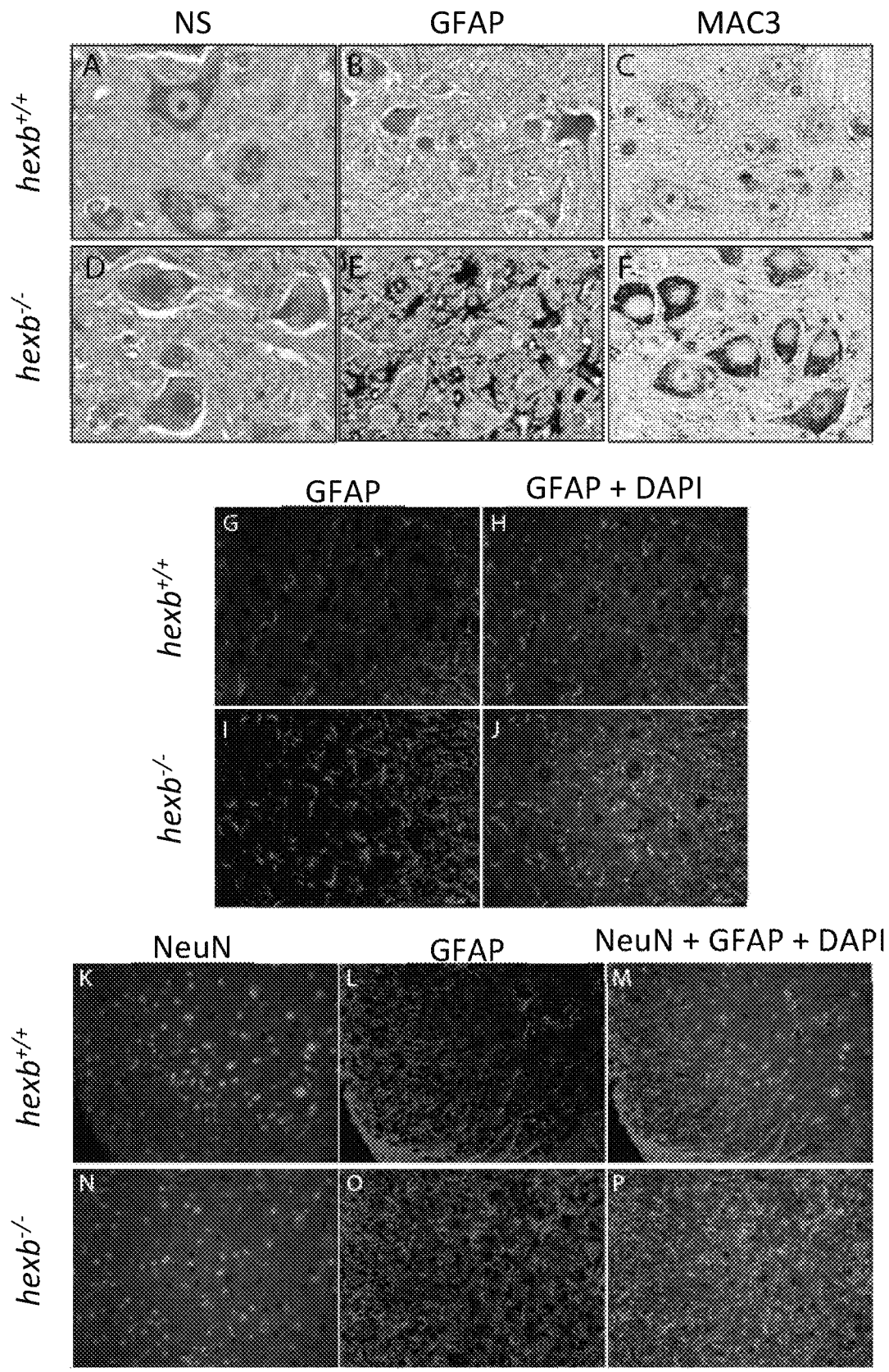

To further document the neuronal variations observed during disease pathogenesis, the area of the cell body ($\mu m^2$) and of the nucleus ($\mu m^2$) were measured (FIG. 4 A,B). As early as 60 days of age significant differences in the area of AHN cell bodies were noted between $hexb^{+/+}$ and $hexb^{-/-}$ mice. The size of the cell bodies of AHNs in $hexb^{-/-}$ mice, increased in parallel with disease progression over time (FIG. 4 C). Nuclear area exhibited an opposite trend in which the area decreased in $hexb^{-/-}$ AHNs temporally (FIG. 4 D). At 60 d of age, the nuclear areas were similar between $hexb^{+/+}$ and $hexb^{-/-}$ AHNs, but a significant reduction was noted at 100 d and 120 d old mice. Lastly, the ratio of nuclear area to cell body area between $hexb^{+/+}$ and $hexb^{-/-}$ AHNs was compared (FIG. 4 E). At 60 d, the ratio was similar between $hexb^{+/+}$ and $hexb^{-/-}$ neurons, but this sharply changed at 80 d where $hexb^{-/-}$ AHNs showed a significant decrease in the nuclear/cell body ratio. This decrease in the ratio persisted from 80 d until the end point of the disease (120 d). These results indicated that lysosomal accumulation begins around 40 d of age and continues to amplify over time. Concurrently, the nuclear shrinkage/condensation observed throughout the disease acts as a potential indicator of apoptosis. These morphological differences accentuate the amount of neuronal damage occurring within $hexb^{-/-}$ mice. It has been previously found that expression of gliosis markers within the spinal cord of $hexb^{-/-}$ mice increased, when compared with $hexb^{+/+}$ mice [21]. More specifically, glial fibrillary acidic protein (GFAP) levels were evaluated, and the number of activated astrocytes was quantified immunocytochemically to assess the level of astrogliosis. In hexb$^{+/+}$ spinal cord sections, most astrocytes showed very low GFAP immunoreactivity (FIG. 1B). In contrast, hexb$^{-/-}$ mice demonstrated overwhelming GFAP immunostaining indicating active astrogliosis within the spinal cord (FIG. 1E). Using immunofluorescence, a striking difference in GFAP activation was highlighted with early pathogenies (60 d) showing very limited astrogliosis while endpoint (120 d) mice again demonstrated a mass amount of astrocyte activation (FIG. 1 G-P). MAC3 was also assessed in the spinal cord sections and demonstrated large differences between hexb$^{+/+}$ and hexb$^{-/-}$ mice. MAC3 showed no reactivity within the anterior horn neurons of the hexb$^{+/+}$ spinal cord (FIG. 1C). Spinal cord neurons in hexb$^{-/-}$ mice showed strong accumulation and staining within the cytoplasm (FIG. 1F). This is representative of the lysosomal accumulation that is a hallmark of lysosomal storage disorders.

Figure 5:
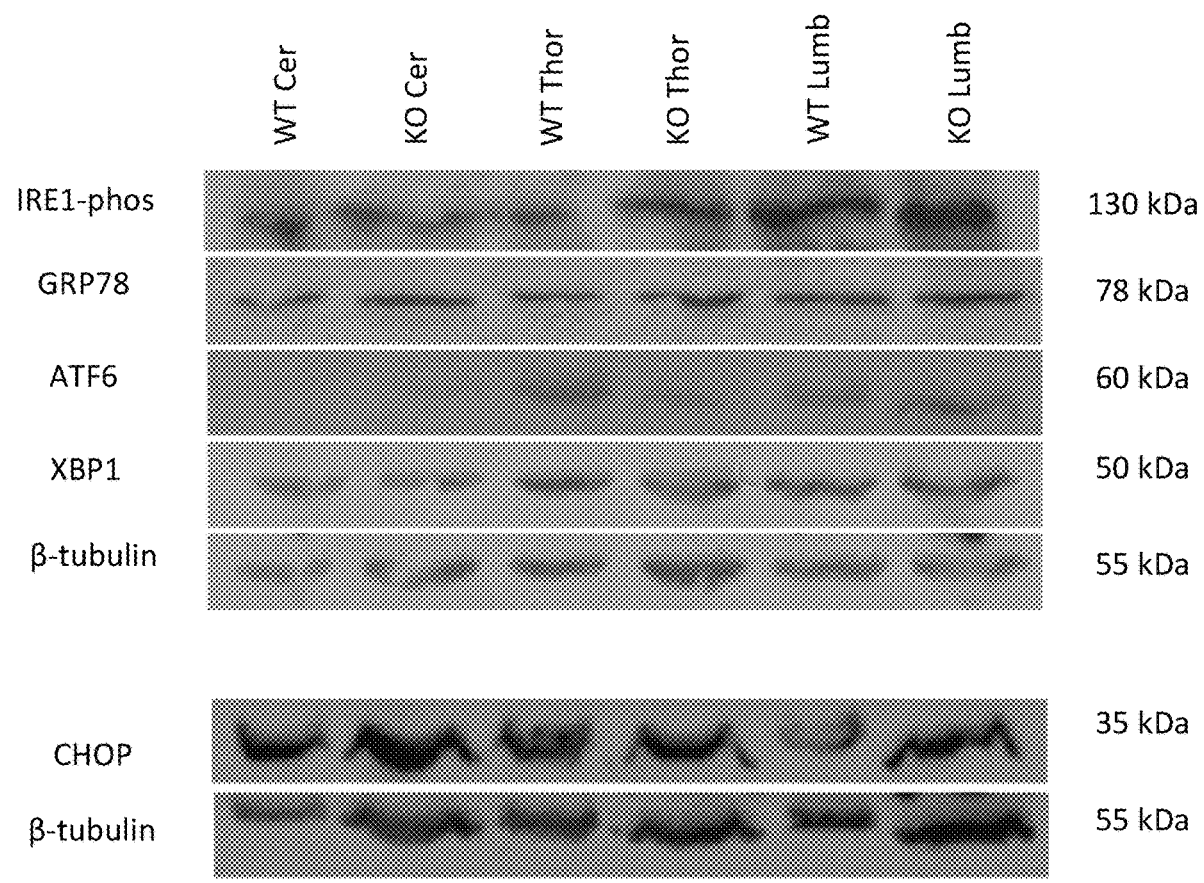

Neurodegeneration is a detrimental consequence observed in SD due to substrate accumulation. The events that connect the lysosomal storage of gangliosides to denervation within the central nervous system (CNS) remain unknown. It was hypothesized that the substrate accumulation within neurons of the spinal cord leads to ER stress induction and neuronal apoptosis. To assess if lysosomal storage leads to the activation and persistence of ER stress in the spinal cord, the global expression levels of multiple ER stress markers, including GRP78, ATF6, XBP1, IRE1-phos, and CHOP were examined using western blot analysis of cervical, thoracic, and lumbar spinal cord lysates from 120-day-old hexb$^{+/+}$ and hexb$^{-/-}$ mice (FIG. 5). It is recognized that expression of UPR markers in the total lysate of the spinal cords which include several cell types, does not accurately represent neuronal expression levels. Nevertheless, differential expression among the distinct regions of the spinal cord was observed. The expression of ER chaperone protein, GRP78, showed comparable expression within the cervical spinal segment of hexb$^{-/-}$ mice relative to hexb$^{+/+}$ mice. Similar trends in expression levels were observed in the thoracic and lumbar spinal segments. Next, phosphorylated IRE-1 showed similar levels of expression in the cervical region and lumbar regions, while the thoracic section of the spinal cord showed increased levels, indicating that the IRE-1/XBP1 pathway is being activated during the late stages of the disease. In addition, ATF6 levels were also elevated within the cervical and lumbar regions of hexb$^{-/-}$ mouse spinal cords with the thoracic section showing a decrease. Furthermore, XBP1, a potent downstream transcription factor regulated by ATF6 and phosphorylated IRE-1, also demonstrated comparable levels within the cervical and lumbar regions in hexb$^{-/-}$ mice. However, XBP1 had reduced expression within the thoracic segment. Lastly, the pro-apoptotic factor CHOP was investigated to determine if severe and prolonged ER stress, which can result in apoptosis, exists within hexb$^{-/-}$ spinal cord segments. Elevated expression levels of CHOP were observed within all three regions of the spinal cord of hexb$^{-/-}$ mice in relation to hexb$^{+/+}$ mice. This suggests that the global ER stress within the cervical and lumbar regions appears to be more severe. Overall, these results demonstrate that ER stress is induced within the spinal cords of hexb$^{-/-}$ mice and that the stress is persistent and severe.

Figure 6:
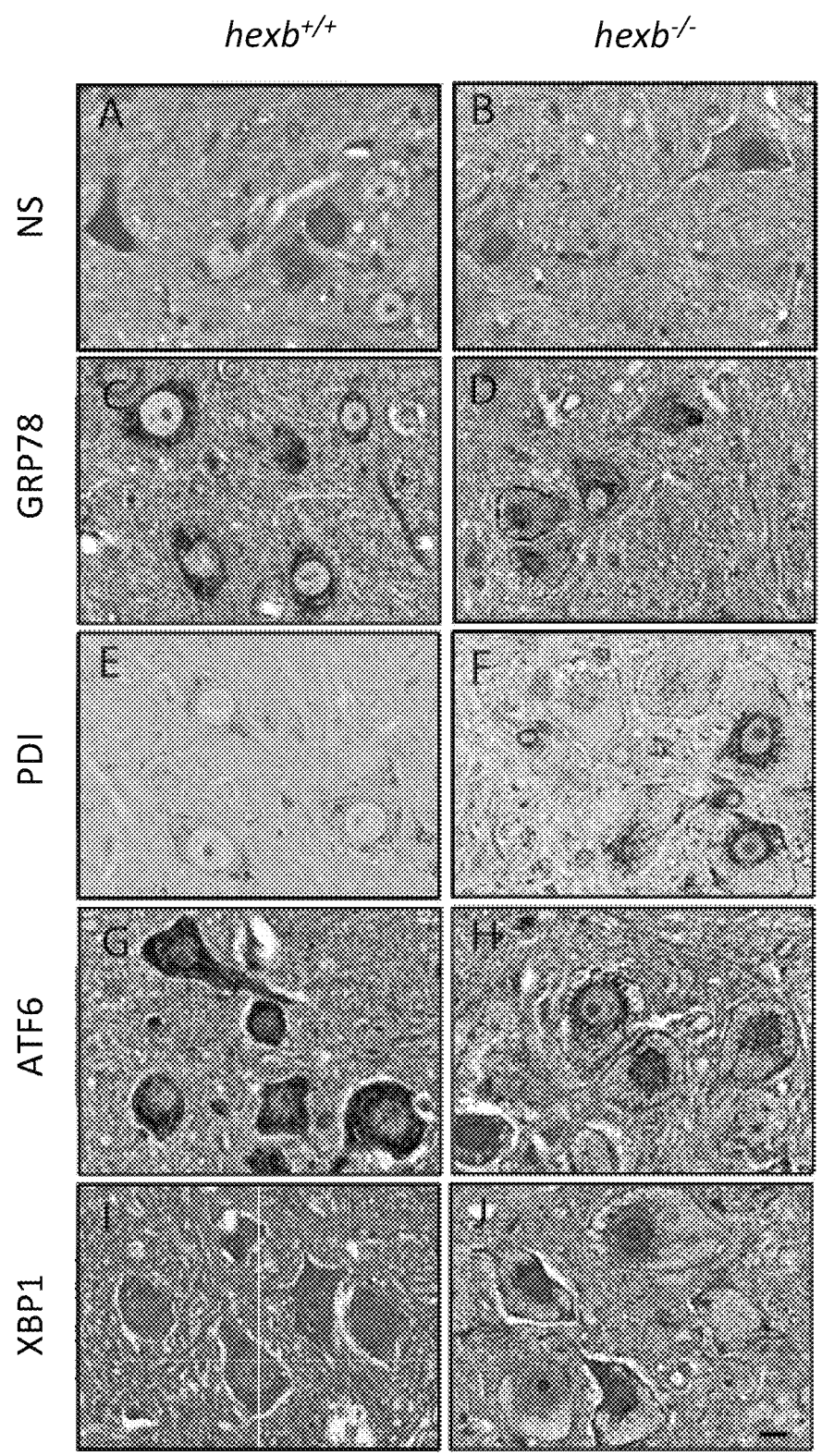
Figure 7:
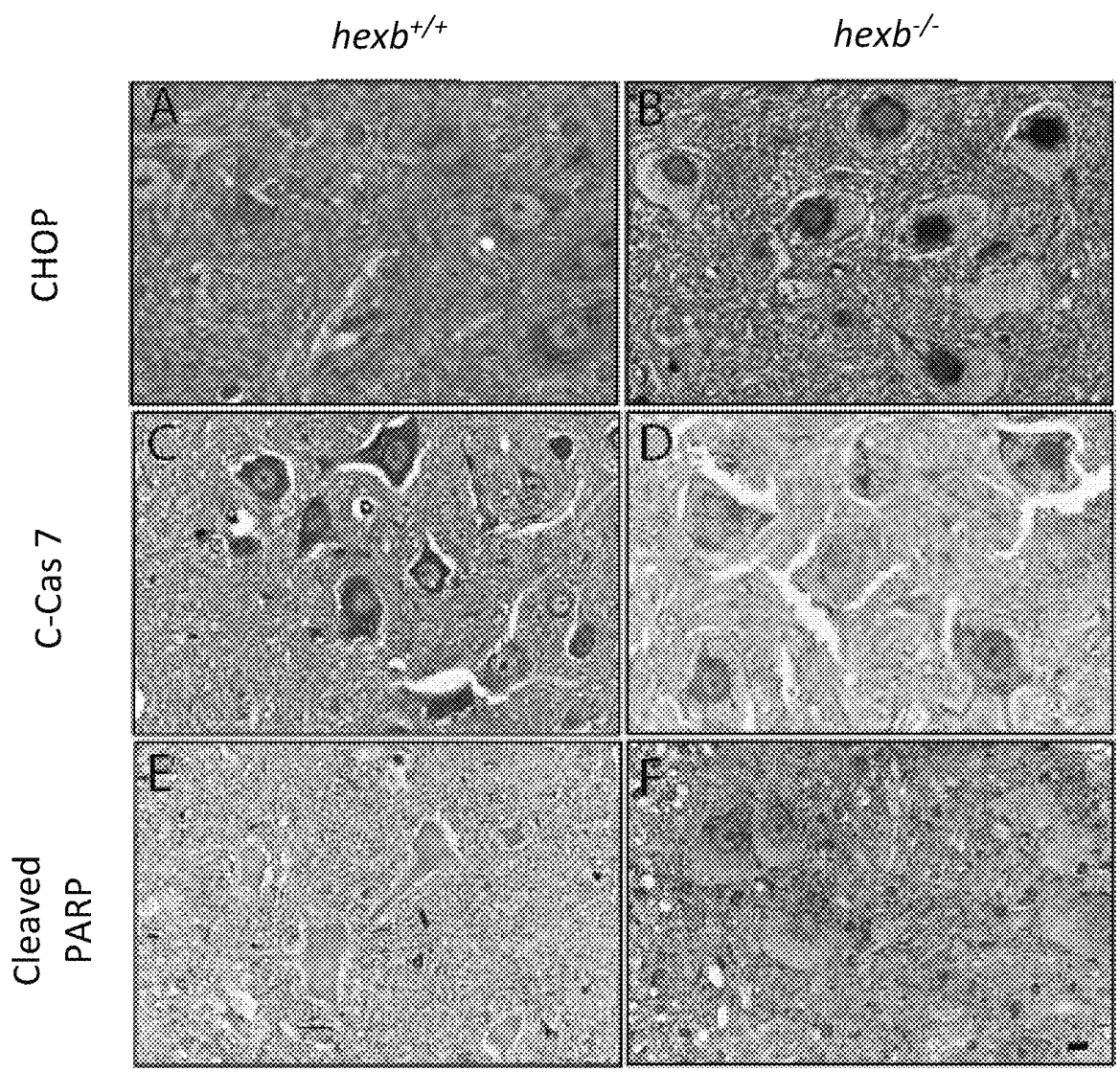
FIG. 7 shows representative immunohistological micrographs of pro-apoptotic, CHOP, and apoptosis inducing markers, cleaved caspase 7 and Cleaved PARP, within the anterior horn motor neurons of 120-day-old hexb$^{+/+}$ and hexb$^{-/-}$ mouse spinal cords in an exemplary embodiment of the application. Scale=10 μm.

The expression analysis using western blots alludes to the occurrence of ER stress in the spinal cord of hexb$^{-/-}$ mice, with interesting interregional variations. In order to examine the expression levels of UPR markers at the cellular level, the immunocytochemical localization of ER stress markers was examined between and within each of the spinal cord regions, specifically in AHNs. Immunocytochemistry was performed on paraffin-embedded sections of spinal cords from 120-day-old hexb$^{-/-}$ and hexb$^{+/+}$ mice using several markers of ER stress: GRP78, PDI, ATF6, XBP1, and CHOP, as well as PARP, a marker of apoptosis (FIG. 6, FIG. 7). A negative control was also included using normal mouse serum as the primary antibody to verify that the staining seen within hexb$^{+/+}$ and hexb$^{-/-}$ spinal cord sections was specific (FIG. 6 A,B). The examination of the expression of these markers spatially within the spinal cord, and their intracellular localization provides insight regarding spinal cord histopathology, and morphological alterations of AHNs, allowing for a more comprehensive understanding of how this disease impacts the neurons.

ER chaperone proteins contribute significantly to the continued maintenance of proper ER functioning through increasing protein folding efficiency, regulating Ca$^{2+}$ homeostasis, and their ability to detect ER stress within the cell (30). GRP78, which is one of the most abundant proteins within the ER, holds the 3 arms of the UPR inactive and is imperative in the activation of the ER stress response (32). In spinal cord sections collected from hexb$^{+/+}$ mice, GRP78 staining was observed in all three regions of the spinal cord with intraregional variability of its dispersal. Within the dorsal horn mild staining was observed, with slightly heavier staining within the intermediate column and anterior horn. Comparing GRP78 immunoreactivity interregionally in wild type mice indicated that the thoracic segment contained elevated staining intensity in comparison to the cervical and lumbar segments. At a cellular level, GRP78 showed a unique punctate cytoplasmic pattern illustrated by the dark spots scattered throughout the cytoplasm (FIG. 6 C). These punctations are known as Nissl bodies which contain rough ER. This type of staining aligns with the functionality of GRP78, as it contributes to the formation of functional proteins, and its intracellular localization within the ER under nonstress conditions. The distinct visibility and vast dispersal of the Nissl bodies within the cytoplasm was noted. In contrast, hexb$^{-/-}$ spinal cord sections showed a decrease in the staining intensity per cell, but the total staining levels in each region of the spinal cord showed an increase in the number of cell types that contain GRP78 staining.

In hexb$^{-/-}$ mice, a modest increase in the amount of immunoreactivity within cells of the dorsal horn of the cervical section was observed when compared to the hexb$^{+/+}$ samples. Sections from hexb$^{-/-}$ mice appeared to show less intense accumulation of GRP78 within the anterior horn in comparison to the hexb$^{+/+}$, potentially due to the extensive change in intracellular localization caused by lysosomal storage and ER stress activation. Supporting this notion, the spinal motor neurons displayed clear localization discrepancies of GRP78 between the hexb$^{+/+}$ and the hexb$^{-/-}$ mice, as well as variation exclusively within the AHNs of hexb$^{-/-}$ mice. Specifically, AHNs present in the cervical spinal section showed staining localized to a halo surrounding the nuclear membrane, while neurons within the thoracic region displayed a combination of diffuse cytosolic and cellular membrane localization (FIG. 6 D). The cytoplasmic staining seen within these knockout neurons was immensely different from the Nissl bodies seen within the hexb$^{+/+}$, as the staining was now diffused throughout the entire cytoplasm and the punctate patterning was no longer present. Overall, the variation in the total amount of staining within the spinal cord sections and the unique cellular localization seen within the hexb$^{-/-}$ sections suggested that ER stress is activated and changes in GRP78 occurred in response.

A second ER resident protein, Protein Disulfide Isomerase (PDI), was also evaluated because of its significant functions within the ER, including disulfide formation and protein folding. PDI in response to stress, like GRP78, has been reported to be upregulated as the cell attempts to reduce the load of misfolded proteins accumulating in the ER. The hexb$^{+/+}$ spinal cord segments showed very minimal staining which was mainly restricted within the anterior horn. PDI exhibited identical intracellular localization as GRP78, with the degree of staining being much less intense for PDI. Nissl bodies were again prevalent throughout the cytoplasm of the AHNs. Due to the less intense nature of PDI's stain, the highly specific sequestration within Nissl bodies was observed with a greater magnitude (FIG. 6 E). In sharp contrast to the hexb$^{+/+}$, the hexb$^{-/-}$ spinal cord sections showed an amplification in the total amount of staining seen within each section. An evaluation of staining dispersal interregionally revealed that the dorsal horn cell population contained the least amount of PDI immunoreactivity in comparison to the intermediate column and anterior horn. Again, hexb$^{-/-}$ spinal cord motor neurons showed a conspicuous shift in the localization and staining intensity in contrast to the intracellular localization seen in hexb$^{+/+}$ AHNs. Neurons showing heavy lysosomal accumulations typically showed PDI localization in a halo around the nucleus (FIG. 6 F). This sequestration pattern, paired with the identical observation seen with GRP78 in hexb$^{-/-}$ motor neurons, suggested that due to the amount of accumulation within the lysosomes, the ER becomes limited against the nuclear membrane creating the formation of the halo encompassing the nucleus. Neurons with a lesser degree of accumulation showed fewer Nissl bodies paired with intense, diffused cytosolic staining, all of which is indicative of PDI upregulation. Taken together, the results of these ER chaperone proteins immunoreactivity and localization within hexb$^{-/-}$ spinal samples provided evidence of increased ER stress activation, alterations in chaperone protein expression, and accentuated substrate accumulation within lysosomes which disrupts organelle intracellular localization.

The ER stress response consists of multiple pathways that work in concert to initiate a variety of downstream cellular events that will either act to protect the cell, i.e., pro-survival, or in the case of severe and prolonged ER stress will result in the triggering of apoptotic events. To begin to dissect this complex process, changes in the immunocytochemical localization of ATF6 and XBP1 were characterized within hexb$^{-/-}$ spinal cords compared to hexb$^{+/+}$ mice. ATF6 is a membrane bound ER protein that is cleaved to turn into a potent transcription factor that stimulates upregulation of XBP1 mRNA expression. XBP1 mRNA is subsequently processed by phosphorylated IRE-1 to create its activated form, which can then enter the nucleus where it acts to upregulate a variety of UPR target genes. Based on the results of GRP78 and PDI immunolocalization within AHNs, it was hypothesized that ATF6 and XBP1 would also demonstrate differences in their localization between hexb$^{-/-}$ and hexb$^{+/+}$ spinal samples indicative of their activation. In the hexb$^{+/+}$ spinal cord sections, ATF6 immunoreactivity was observed throughout each of the three regions, with more intense staining focused within the AHNs and dorsal horn. Between the three sections, the lumbar region showed marginally less staining in comparison to the cervical and thoracic regions. Within the AHN specifically, equally diffuse and intense cytoplasmic staining was observed (FIG. 6 G). This localization pattern indicated the presence of inactive, ER bound ATF6 within the cell. The hexb$^{-/-}$ spinal sections demonstrated decreased amounts of overall staining, especially within the cervical region. Upon examination of intracellular localization, a marked change from cytosolic, in the hexb$^{+/+}$ to primarily nuclear accumulation within the AHNs of hexb$^{-/-}$ mice was noted (FIG. 6 H). Nuclear staining of ATF6, which is a conformational indicator that ATF6 was cleaved, indicated that it was now functioning as a transcription factor, and that the UPR was instigated within these spinal cord neurons. Interestingly and unique to ATF6, in all three regions there were enhanced levels of staining specifically in the dorsal horn. Next, XBP 1 localization and immunoreactivity discrepancies between hexb$^{+/+}$ and hexb$^{-/-}$ mice were examined. Spinal sections of hexb$^{+/+}$ mice showed XBP1 immunoreactivity dispersed throughout each region, with a decline in staining intensity moving posteriorly through the section. The AHNs mainly exhibited cytosolic staining with a discrete number of cells presenting with nuclear staining (FIG. 6 I). Cytosolic staining is indicative of inactivated XBP1, which was expected under homeostatic cellular conditions. In contrast, the knockout spinal cord sections appeared to have a lower amount of total staining within the regions, with the ventral horns displaying more concentrated XBP1 staining. The AHNs clearly showed lipid accumulation within the lysosomes but more importantly they exhibited salient nuclear XBP1 accumulation that was not detected in the hexb$^{+/+}$ spinal cord samples (FIG. 6 J). XBP1 cleavage, which activates its ability to regulate transcription of UPR target genes, is completed after the induction of ER stress. This allows for the translocation of XBP1 to the nucleus, which was the localization pattern observed in the AHNs of hexb$^{-/-}$ mice. Activated ATF6 and XBP1, both with clear nuclear localization within the hexb$^{-/-}$ spinal cord sections, provided further evidence that ER stress response was highly activated and that at least 2 of the 3 UPR signaling mechanisms were involved.

The intensity of the ER stress observed within the spinal cord of hexb$^{-/-}$ mice, could potentially result in neuronal apoptosis. This has been determined by evaluating the localization of CHOP, a pro-apoptotic factor, as well as cleaved caspase 7 and cleaved PARP, potent regulators of apoptosis (FIG. 7). CHOP is an important downstream factor to explore because it plays a vital role in the cells decision to undergo apoptosis and its expression can be regulated by all 3 arms of the UPR. All three wild type hexb$^{+/+}$ spinal sections, at low magnification, appear negative for CHOP staining. Upon examination of AHNs specifically, it was noted that a small number of neurons had cytosolic staining or, in a few rare cases, nuclear staining, otherwise most other AHNs were devoid of CHOP immunoreactivity (FIG. 7 A). In contrast, hexb$^{-/-}$ mice spinal cords sections showed strong CHOP immunostaining. Within the cervical, thoracic, and lumbar regions there was a very sharp increase in the total number of cells exhibiting CHOP immunoreactivity in all intraregional locations. There was also a dramatic difference in the intracellular localization of CHOP in AHNs. These neurons showed strong accumulation in the nucleus resulting in intense staining (FIG. 7 B). The morphological effects of lipid accumulation, such as engorged structures, ER halos around the nucleus, and loss of cell membrane integrity were quite noticeable in the AHNs. This type of accumulation suggests that there had been prolonged ER stress within these cells and CHOP had been invoked. To expand the understanding of the differences in CHOP expression between hexb$^{+/+}$ and hexb$^{-/-}$ mice, the number of nuclear CHOP positive cells within the anterior horn of spinal cord sections were quantified. This was completed by counting the total number of cells within the anterior horn of the cervical, thoracic, and lumbar regions, that presented with strictly nuclear CHOP staining. These results provide evidence that there are interregional differences within the spinal cord and that the thoracic and lumbar regions, at end point, exhibit slightly stronger signs of apoptosis, demonstrated by the augmentation of cells containing nuclear CHOP staining. A potent inducer of apoptosis is cleaved caspase 7 (c-Cas7), an executioner caspase, which, upon its cleavage, becomes activated and localizes to the nucleus where it processes and activates PARP, a signature of cell-death in neurodegeneration. Therefore, its immunohistological localization was evaluated and expression between 120 d old hexb$^{+/+}$ and hexb$^{-/-}$ mice. In hexb$^{+/+}$ samples, ultimately no staining was observed throughout all three regions of the spinal cord. AHNs were negative for staining except for a few cells which presented with weak nuclear staining (FIG. 7 C). On the contrary, hexb$^{-/-}$ mice exhibited differential levels of expression. The staining was widely dispersed within and between each region of the spinal cord and AHNs of each section presented with clear, intense nuclear accumulation of c-Cas7 (FIG. 7 D). Obvious engorgement of AHNs and disruption in cellular integrity can be observed concurrently with this nuclear localization and activation of c-CAS7. The striking difference of c-CAS7 immunoreactivity between hexb$^{+/+}$ and hexb$^{-/-}$ mice highlights a novel mechanism of neurodegeneration in SD. Lastly, as an evaluation of the prevalence of apoptosis within the spinal cord of hexb$^{-/-}$, the immunoreactivity of cleaved PARP was examined. Cleaved PARP staining was not generally observed within hexb$^{+/+}$ spinal section. The vast majority of spinal motor neurons located within the anterior horn exhibited no staining, which was expected under homeostatic conditions (FIG. 7 E). The hexb$^{-/-}$ sections, in contrast, showed an increase in the global staining of cleaved PARP throughout all regions of the spinal cord. Specifically, the localization of cleaved-PARP staining within the AHNs of hexb$^{-/-}$ was intense and strictly nuclear (FIG. 7 F). This exclusively nuclear localization of cleaved PARP indicated it had been cleaved and the apoptotic pathway had been activated. Overall, the results observed, strongly support the notion that PARP is being activated as a downstream factor in response to lysosomal accumulation and potentially ER stress within the spinal cord of hexb$^{-/-}$ mice. This in turn results in the induction of apoptotic pathways which can account for the drastic neurodegeneration seen in this disease.

Following the identification of ER stress as a major mechanistic pathway involved in the terminal aspect of SD, the question as to how does the induction ER stress and the UPR change developmentally throughout the disease emerged. The above data indicated that a mass neuronal death occurs during the progression of SD; however, the timeline of these events during development and what factors are playing significant roles required further investigation. The relationship between SD pathology, UPR activation, and symptom onset/progression was evaluated at different ages of the SD mouse model.

In continuation of the observations seen with the immunostaining at 120 d, the immunocytochemical localization of ER stress marker was examined developmentally throughout the progression of SD. This analysis focused on the intracellular localization of these markers, specifically within AHNs. Immunocytochemistry was performed on paraffin-embedded spinal cords sections from 60, 80, and 100-day-old hexb$^{-/-}$ and hexb$^{+/+}$ mice using several markers of ER stress: GRP78, ATF6, XBP1, and CHOP, as well as cleaved caspase 7 and cleaved PARP; the latter two are markers of apoptosis. The examination of the expression of these markers spatially within the spinal cord, and their intracellular localization provides insight regarding mechanistic pathways which contribute to the pathology of SD, as well as morphological alterations of AHNs, allowing for a more comprehensive understanding of how this disease impacts neurons within the spinal cord.

Figure 8:
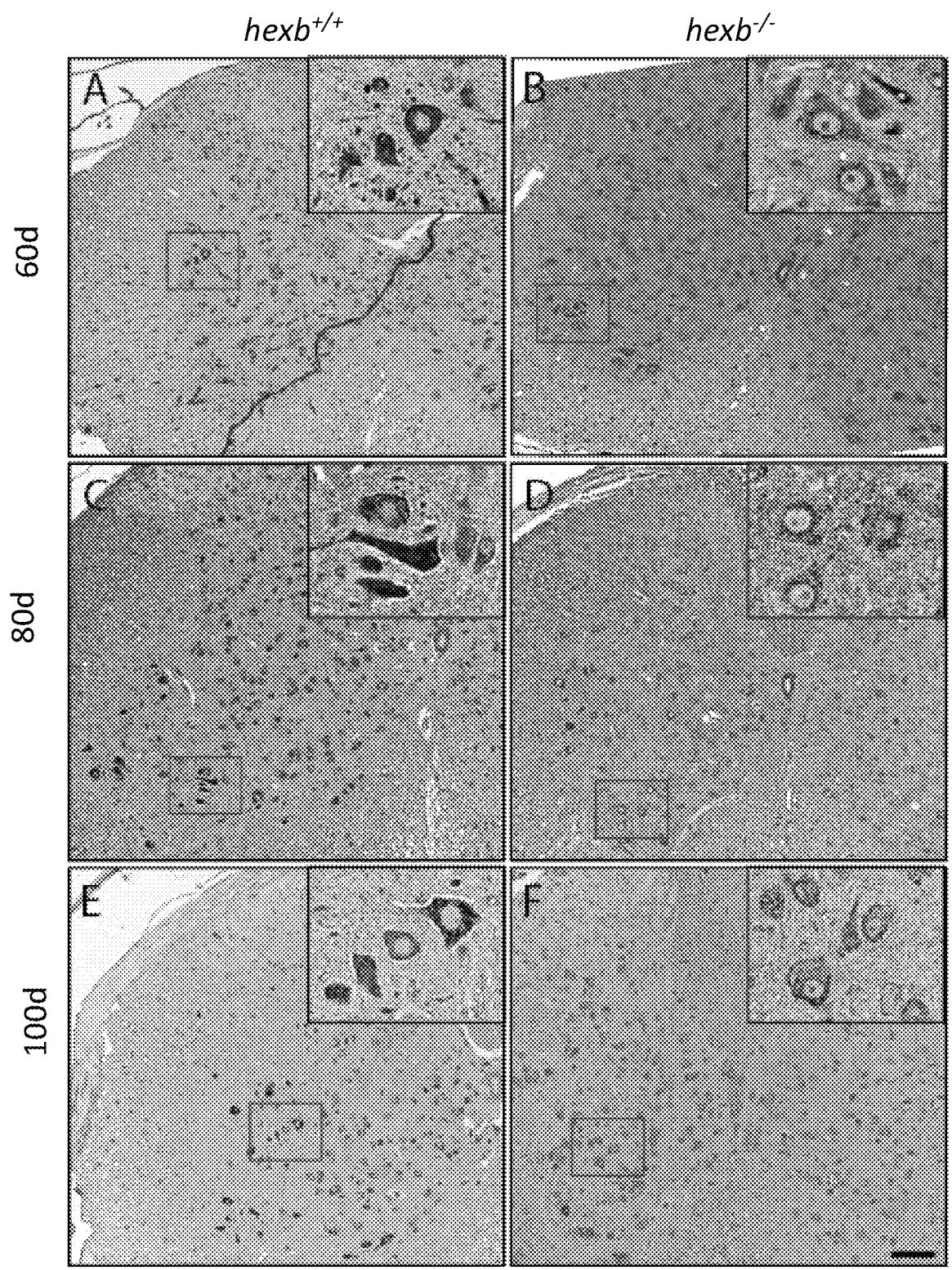
FIG. 8 shows representative immunohistological micrographs of resident endoplasmic reticulum chaperone Grp78 within the cervical spinal cord region of 60 d (A-B), 80 d (C-D), and 100 d (E-F) old hexb$^{+/+}$ and hexb$^{-/-}$ mice in an exemplary embodiment of the application. Scale bar=100 μm.

As previously mentioned, Grp78 is a widely abundant ER chaperone protein that plays a role in sensing and responding to ER stress. Under homeostatic conditions Grp78 holds the three arms of the UPR inactive. In hexb$^{+/+}$ spinal cord samples Grp78 was present within all three regions at 60, 80, and 100-days (FIG. 8 A,C,E). Similar to the 120-day findings, the intraregional dispersion varied at every age. The posterior horn had lower levels of staining when compared to the intermediate column and the anterior horn. When examined at the cellular level, Grp78 continued to exhibit unique punctate cytoplasmic sequestration that was observed in the 120 d hexb$^{+/+}$ sections. The distinct visibility of Nissl bodies within the cytoplasm and dispersed staining pattern was representative of the functional role of Grp78 within the ER during homeostatic conditions. The intensity and pattern of staining appeared consistent across the various ages. This was in sharp contrast to the hexb$^{-/-}$ sections which show GRP78 tapering off following the course of disease progression.

Within 60 d of age, sections of the hexb$^{-/-}$ spinal cords showed a mild reduction in immunoreactivity but many AHNs presented with heavy, punctate, ER staining (FIG. 8 B). The cervical and thoracic regions showed slight variation in the cytosolic dispersal of Grp78, with some neurons showing, loss of the highly specific punctate pattern and begin to demonstrate more diffuse staining. Overall, at this age the knockout AHNs still closely resemble the staining seen within the neurons of the wild type mice. This observation does not hold in older mice. At 80 d, there is a sharp decline in the intensity of the Grp78 immunostaining in the hexb$^{-/-}$ sections across all regions of the spinal cord (FIG. 8 D). Consistent with this notion, the spinal motor neurons showed clear incongruities in localization of Grp78 between the hexb$^{+/+}$ and hexb$^{-/-}$ mice, as well as variation specifically within the AHNs of hexb$^{-/-}$ mice. During ER stress, the role of Grp78 becomes highly important to assist in the restoration of homeostatic conditions and therefore can result in a diverse range of intracellular localizations. AHNs present across all three regions of the spinal cord displayed immunostaining localized to a halo surrounding the nuclear membrane, similar to the staining pattern seen in the 120-day samples. Note that AHNs within the cervical segments of the spinal cord predominantly displayed staining within the ER halo surrounding the nucleus while the thoracic and lumbar neurons highlighted a combination of cell surface and diffuse cytosolic Grp78 staining. Note that the cytoplasmic staining seen within the hexb$^{-/-}$ neurons was drastically different from the Nissl bodies present in the hexb$^{+/+}$. The staining seen was more diffused throughout the entirety of the cytoplasm with a loss of the distinct punctate pattern noted in the wild type. Similar staining distribution was seen within the 100 d sections (FIG. 8 F). The hexb$^{-/-}$ samples exhibited a widely dispersed cytosolic staining with several neurons showing strong staining within the ER halo and at the cell membrane, while the classic intense punctate, immunolabeling was observed in hexb$^{+/+}$ sections. Note that the drastic reduction in immunostaining intensity between hexb$^{+/+}$ and hexb$^{-/-}$ was still observed, as previously noted in the 80 d group.

Overall, the relocalization of Grp78 within the hexb$^{-/-}$ spinal segments is indicative of its activation caused by ER stress induction, which starts as early as 60 d. A drastic change in immunostaining intensity between 60 d and 80 d was also observed, suggesting a potential change in Grp78 abundance and mechanistic ability, as well as a loss of ER functionality. Further supporting this notion is the formation of an ER halo surrounding the nuclear envelope beginning at 60 d and becoming increasingly evident by 80 d and 100 d. This indicates a disruption in the ER network due to lysosomal accumulation, causing the ER to be pushed against the nucleus, starting early in disease pathogenesis. This disruption, in combination with an apparent reduction in Grp78, can result in a whole host of consequences involving cellular function and homeostatic regulation all of which can potentiate ER stress and UPR activation.

Figure 9:
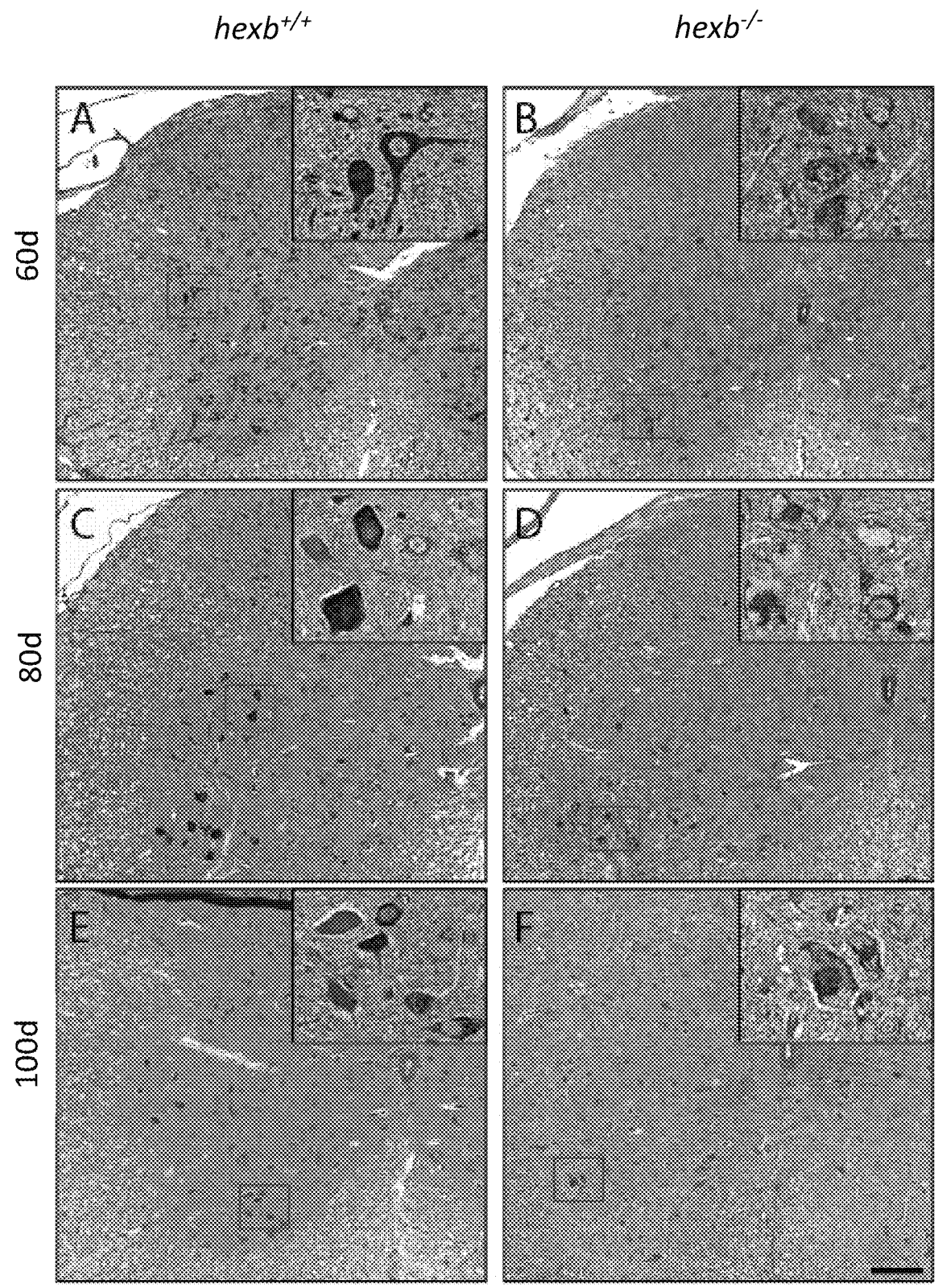
FIG. 9 shows representative immunohistological micrographs of ATF6, within the cervical spinal cord region of 60 d (A-B), 80 d (C-D), and 100 d (E-F) old hexb$^{+/+}$ and hexb$^{-/-}$ mice in an exemplary embodiment of the application. Scale bar=100 μm.

The UPR and ER stress is a highly complex process with multiple cascades working differentially over time to help restore homeostasis or in cases of chronic stress, induce apoptosis. After identifying the activation of ATF6 and XBP1 during the terminal stage of SD, expression of these markers was characterized at different ages during disease development. In hexb$^{+/+}$ spinal sections, ATF6 immunostaining was widespread throughout all three regions and within each region, with more intensive staining occurring in the AHNs. This pattern of staining was consistent in all hexb$^{+/+}$ samples across 60 d, 80 d and 100 d sections (FIG. 9 A,C,E). Between the three regions, the cervical and thoracic segments showed marginally more staining in comparison to the lumbar segment. The intracellular localization, specifically within the AHNs, revealed equally diffused, punctate, intense, cytosolic staining. This observed pattern indicated that inactive, ER bound ATF6 is present within the cells of hexb$^{+/+}$ spinal samples. On the other hand, the hexb$^{-/-}$ spinal sections exhibited some contrasting immunostaining that changed during disease development and age. A pattern indicative of ER bound, or Golgi retained ATF6 was observed within the 60 d hexb$^{-/-}$ spinal cords. Albeit staining intensity was notably decreased compared to the hexb$^{+/+}$ sections, it remained in the reticular structures within the cytosol (FIG. 9 B). Interestingly, AHNs displayed enhanced levels of staining in comparison to cells within the intermediate zone and posterior horn. Upon examination of 80 d hexb$^{-/-}$ samples, a translocation and redistribution of ATF6 immunostaining was noted from strictly reticular cytosolic to partially cytosolic and predominantly nuclear (FIG. 9 D). Despite some staining remaining within the cytosol, the distribution of cytosolic immunolabeling changed from diffuse and punctate to clustered around the nucleus in an ER halo. Having a significant proportion of ANHs exhibiting nuclear staining, acts as a conformational indicator that ATF6 has been cleaved and is translocated to nucleus. Furthermore, the staining intensity displayed an additional reduction between 80 d hexb$^{-/-}$ samples and age matched hexb$^{+/+}$ sections but also between 60 d hexb$^{-/-}$ and 80 d hexb$^{-/-}$ samples which signified that ATF6 begins to taper off in parallel with disease progression. Similarly, 100 d old spinal cord sections also showed a combination of ER halo and nuclear staining, with a large proportion of staining focused within AHNs (FIG. 9 F). These results indicated a transient activation and translocation of ATF6 between 80-100 d of age. In summary, the mechanistic shift between ER associated/Golgi retained ATF6 in 60 d hexb$^{-/-}$ spinal cord segments to the combinatorial labeling seen in 80 d hexb$^{-/-}$ and 100 d hexb$^{-/-}$ samples highlighted the differential expression of ATF6 and, by extension, of ER stress temporally and spatially in SD mouse model.

Figure 10:
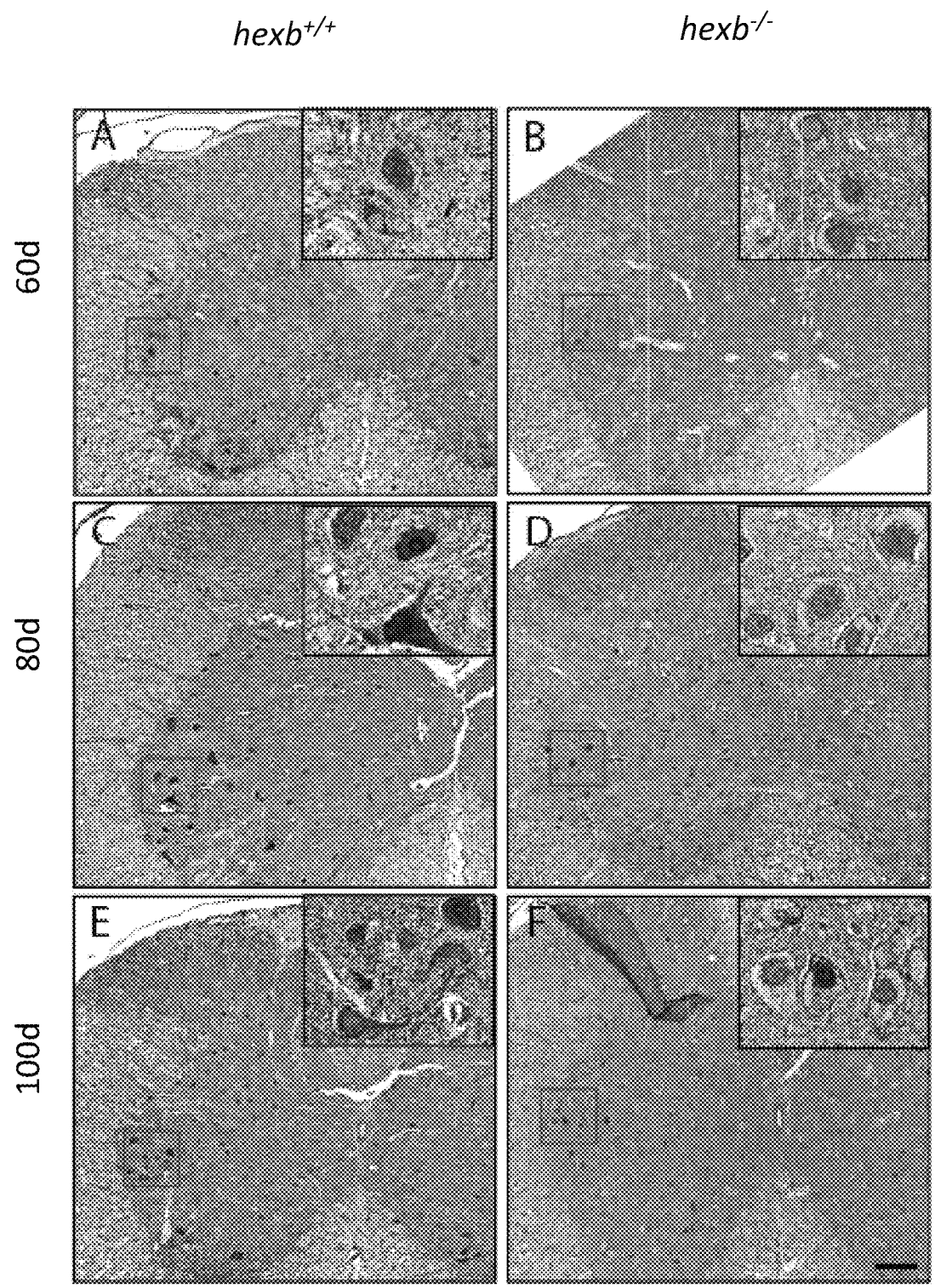
FIG. 10 shows representative immunohistological micrographs of XBP1, a downstream target of multiple UPR arms, within the cervical spinal cord region of (A-B), 80 d (C-D), and 100 d (E-F) old hexb$^{+/+}$ and hexb$^{-/-}$ mice in an exemplary embodiment of the application. Scale bar=100 μm.

To extend the investigation to downstream targets of ATF6 and IRE1, the temporal and spatial expression of XBP1 was further examined. Spinal cords from 60-day old hexb$^{+/+}$ mice revealed minimal levels of cytosolic immunoreactivity across many cell types in all three regions (FIG. 10 A). A reduction in staining intensity was observed toward the posterior region of each section. The AHNs exhibited the heaviest cytosolic staining with very few cells displaying weak nuclear staining. This staining pattern indicated the presence of inactive or uncleaved XBP1 which is a direct conformation of the inactivity of IRE1, therefore demonstrating a lack of ER stress and UPR activation which was expected in wild type conditions. Similar findings were noted in the remaining 80 d and 100 d hexb$^{+/+}$ spinal cord samples (FIG. 10 C,E). In contrast, the hexb$^{-/-}$ mice revealed differential staining patterns, localization and expression levels in the various ages examined. At 60 d old hexb$^{-/-}$ mice, all three regions of the spinal cord showed similar levels of total staining when compared to hexb$^{+/+}$ samples. The same dispersal pattern was also maintained in which staining decreased moving from the ventral horn to the dorsal horn. However, the AHNs showed a striking translocation of XBP1 from the cytosol into the nucleus which was not noted in the hexb$^{+/+}$ spinal sections (FIG. 10 B). Translocation of XBP1 was also observed within cells, most prominent in the AHNs, of 80 d and 100 d hexb$^{-/-}$ mice (FIG. 10 D,F). Comparably to the 60 d sections, the 80 d hexb cervical and lumbar regions showed a marginal increase in overall staining while the thoracic region exhibited a salient increase in immunoreactivity in comparison to hexb$^{+/+}$ segments. On the contrary, at 100 d, the hexb$^{-/-}$ spinal cord sections appeared to show a decrease in the total staining present, as well as a change in the distribution of the staining. The AHNs within the cervical region had minimal staining or were completely negative, with most nuclear labeled cells localized in the intermediate zone (FIG. 10 F). Heavy nuclear staining was still observed within the AHNs of the thoracic and lumbar sections. Comparatively, the 80 d samples emerged to represent the peak of XBP1 expression and nuclear translocation throughout the spinal cord of hexb$^{-/-}$ mice. Nuclear XBP1, which is regulated by IRE1, solidifies the role of this signaling cascade in the induction ER stress during the pathogenesis of SD.

The identification of activated ER stress markers such as ATF6 and XBP1 as early as 60 d within the spinal cords of hexb$^{-/-}$ mice posed the question whether neuronal apoptosis occurs much earlier than the expected end point of 120 days of age. The expression and localization of CHOP, a pro-apoptotic transcription factor, and two markers of apoptosis: cleaved PARP, and cleaved caspase 7 was evaluated.

Figure 11:
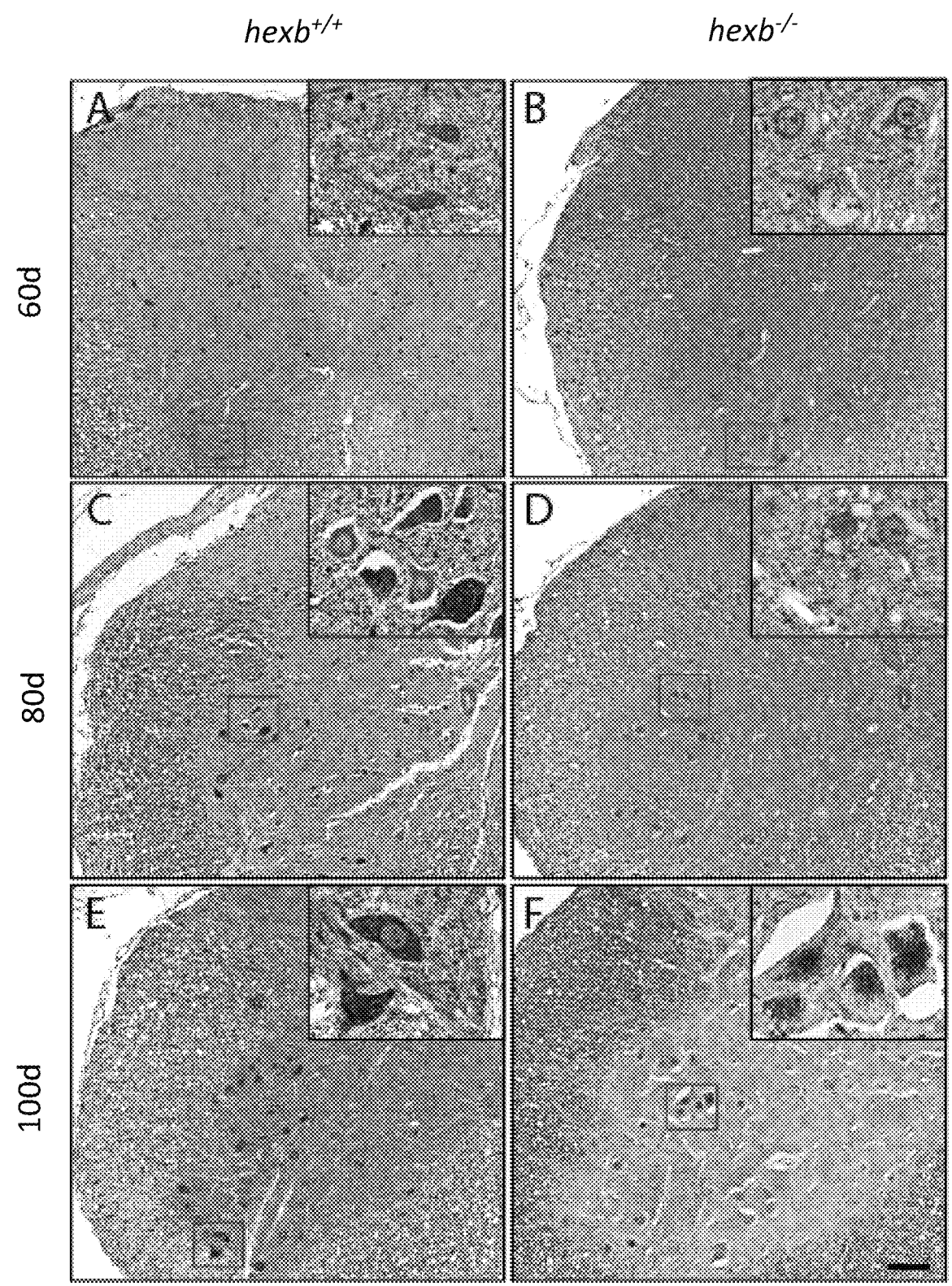
FIG. 11 shows representative immunohistological micrographs of CHOP, within the cervical spinal cord region of 60 d (A-B), 80 d (C-D), and 100 d (E-F) old hexb$^{+/+}$ and hexb$^{-/-}$ mice in an exemplary embodiment of the application. Scale bar=100 μm.

CHOP is a key regulator in cell fate determination as it plays a vital role in the apoptotic decision of the cells. Cytosolic immunostaining of CHOP, predominantly within AHNs, was observed in all three regions of hexb$^{+/+}$ spinal sections, with most other cell types devoid of CHOP immunoreactivity (FIG. 11 A,C,E). CHOP is ubiquitously expressed at low levels and therefore cytosolic expression was expected under homeostatic conditions. This localization pattern was seen consistently between regions but also across all three ages of hexb$^{+/+}$ mice. In contrast, hexb$^{-/-}$ spinal sections demonstrated a striking translocalization of CHOP to the nucleus. Interestingly, at 60 days several AHNs were already exhibiting nuclear staining ranging from light to quite intense and upon further evaluation, focals were noted in several of the stained nuclei (FIG. 11 B). Global immunoreactivity levels within each spinal cord region were marginally less to that of the hexb$^{+/+}$ sections and were comparable between the segments. Similarly, 80-day hexb$^{-/-}$ spinal sections demonstrated a clear nuclear localization of CHOP with conspicuous intra-nuclear punctate staining (FIG. 11 D). By 100 d, the AHNs showed clear morphological characteristics of lipid accumulation and distress. This was accompanied by nuclear immunostaining of CHOP, as seen in earlier ages (FIG. 11 F). Immunoreactivity was more concentrated within the anterior and posterior horns, with lesser amounts in the intermediate zone. Interregional differences were also apparent, as the cervical and thoracic regions appeared to exhibit lower numbers of CHOP positive AHNs, suggesting a peak in CHOP activation around 80 d of age, while the lumbar region maintained dominant staining in the AHNs. To further elucidate the differences in CHOP expression and localization temporally between hexb$^{+/+}$ and hexb$^{-/-}$ mice, the number of nuclear CHOP positive cells was quantified within the anterior horn of spinal cord samples. This was completed by counting the total number of cells within a defined area of the anterior horn of the cervical, thoracic, and lumbar regions, that presented with strictly nuclear CHOP staining. Three independent sets of spinal cords were evaluated, the numbers were standardized as cells/mm$^2$. Within the cervical segment across all ages, there was a clear increase in the number of nuclear CHOP positive cells located within the anterior horn of hexb$^{-/-}$ spinal cords compared to hexb$^{+/+}$ (FIG. 2 D). The peak of CHOP activation in this region was noted at 80 d, while all other ages showed similar numbers between hexb$^{-/-}$ samples. The thoracic region only showed a slight variation in the activation pattern of CHOP in that all ages showed comparatively similar numbers between hexb$^{-/-}$ sections but exhibited significant differences between hexb$^{+/+}$ and hexb$^{-/-}$ samples (FIG. 2 E). Finally, the lumbar section revealed similar overall numbers of cells displaying nuclear CHOP between hexb$^{-/-}$ mice but again demonstrated significant increases across all ages between hexb$^{+/+}$ and hexb$^{-/-}$ samples (FIG. 2 F). However, a peak point of CHOP activation within the SD lumbar sections appeared at 100 d of age. At endpoint (120 d), all three regions had a significant increase in the number of nuclear CHOP positive cells (FIG. 2 D-F). More specifically, the thoracic and lumbar regions of the hex$^{-/-}$ spinal cord presented with the most dramatic increase, while the cervical section showed a marginally lower increase in comparison.

Figure 12:
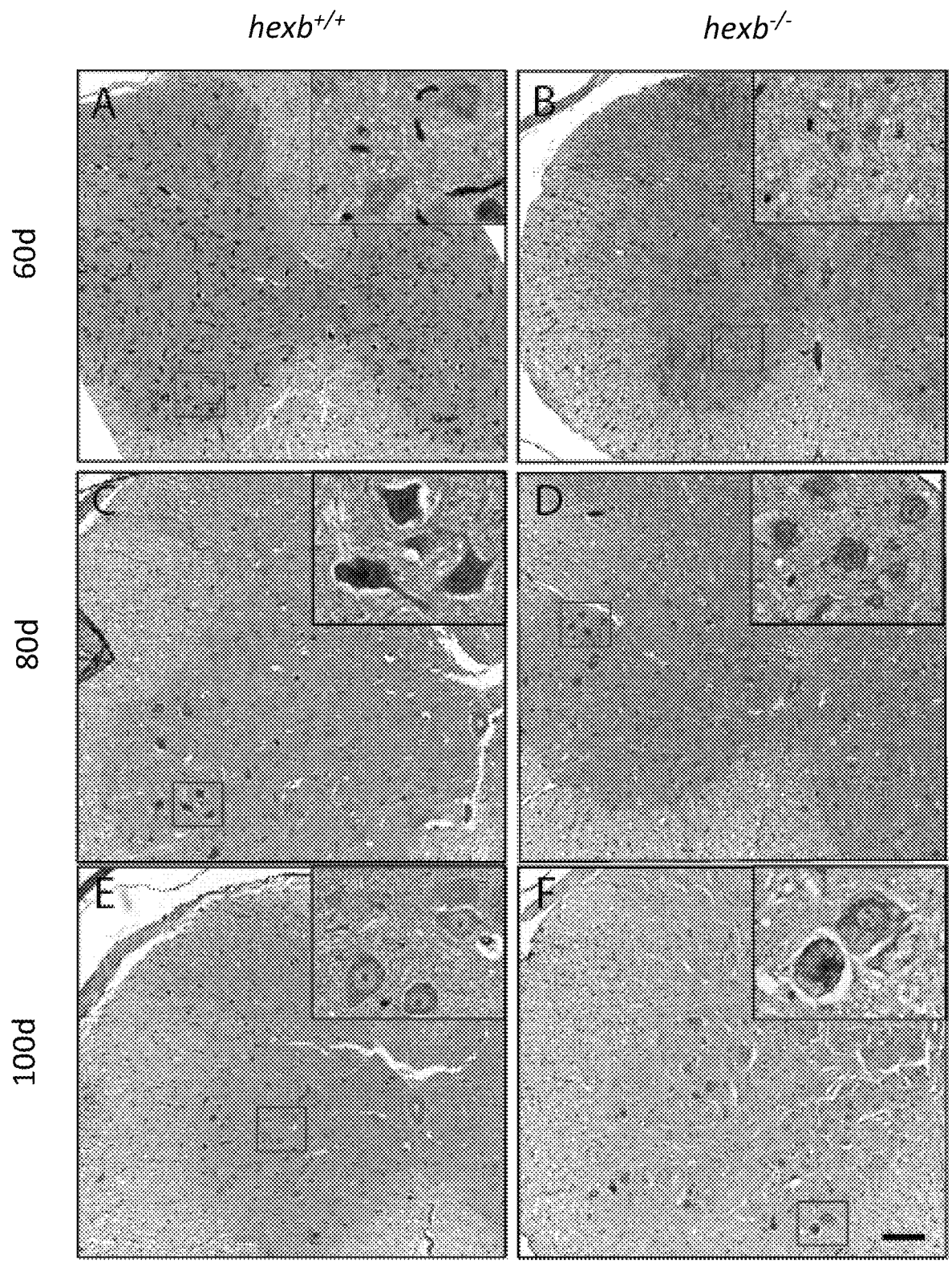
FIG. 12 shows representative immunohistological micrographs of cleaved caspase 7 (c-Cas7), an executioner caspase known to be a marker of cellular apoptosis, within the cervical spinal cord region of 60 d (A-B), 80 d (C-D), and 100 d (E-F) old hexb$^{+/+}$ and hexb$^{-/-}$ mice in an exemplary embodiment of the application. Scale bar=100 μm.

These two vital potentiators of ER stress have been identified as activated at terminal stages of SD. Therefore, the intracellular localization of these apoptotic markers temporally in the spinal cords of hexb$^{+/+}$ and hexb$^{-/-}$ was evaluated, to determine a timeline of the mass neuronal death known to be associated with SD pathology. Within wildtype hexb$^{+/+}$ sections, the vast majority of AHNs were negative for cCas7 immunoreactivity (FIG. 12 A,C,E). This was true across all ages, with the most notable cytosolic staining at 100 d. Conversely, the hexb$^{-/-}$ spinal cord segments demonstrated clear nuclear localization of cCas7, which is an indication of its activation. Within the 60 d SD spinal cords, AHNs and other neurons clearly expressing nuclear cCas7 (FIG. 12 B) was observed. This staining pattern persisted at 80 d and 100 d, but a small pool of AHNs which were negative for staining were also observed (FIG. 12 D,F). Throughout the pathogenesis of the disease, a decrease in the total immunostaining of c-Cas7 within each region of SD mice was noted. Marginal variations began at 80 d and were followed by a continual decline throughout 100 d of age and into the terminal stages of the disease, as previously mentioned. Although a decrease was seen in total staining of cCas7 among hexb$^{-/-}$ spinal cords, the differences in the presence of nuclear cCas7 between hexb$^{+/+}$ and hexb$^{-/-}$ samples of all ages were very clear and statistically significant. To further elucidate the differences in cCas7 expression and its variation in localization temporally between hexb$^{+/+}$ and hexb$^{-/-}$ mice, the number of nuclear cCas7 positive cells within the anterior horn of spinal cord samples was quantified. Within the cervical, thoracic, and lumbar regions, a predefined area of the anterior horn was established and the total number of that presented with strictly nuclear cCas7 staining were counted (FIG. 2 G-I). Three independent sets of spinal cords were evaluated, the numbers were standardized as cells/mm$^2$. Consistent trends in the amount of nuclear cCas7 positive cells present were seen across all three regions of hexb$^{-/-}$ spinal cords. Interestingly, the peak of cCas7 was seen at 60 days, which is far earlier than previously hypothesized, and this was true for all three regions. Subsequent deterioration of activated cCas7 cell numbers was seen in a stepwise manner throughout the remainder of the ages. Levels in the cervical region at 60 d and 80 d were significantly higher in hexb$^{-/-}$ samples in comparison to hexb$^{+/+}$ sections, while variations at 100 d and 120 d were not. This finding remained consistent for both the thoracic and lumbar sections and parallels the mass neuronal loss seen at the later ages. These observations clearly demonstrate the immense activation of c-Cas7 early during disease progression and provides evidence that this mechanism of apoptosis occurs much earlier than expected leading toward neuronal degeneration prominent in the SD mouse model.

Figure 13:
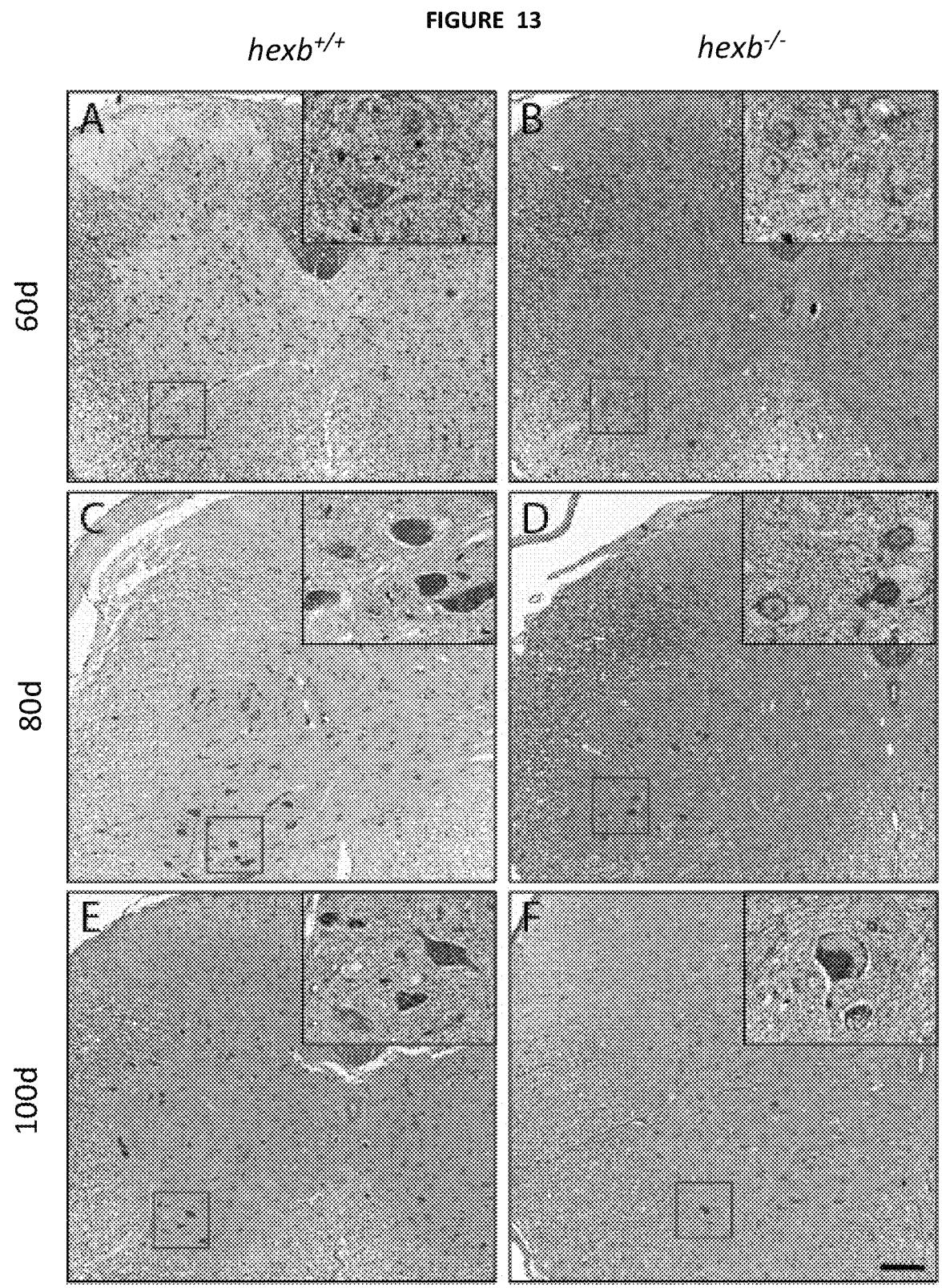
FIG. 13 shows representative immunohistological micrographs of cleaved PARP, a known marker of apoptosis, within the cervical spinal cord region of 60 d (A-B), 80 d (C-D), and 100 d (E-F) old hexb$^{+/+}$ and hexb$^{-/-}$ mice in an exemplary embodiment of the application. Scale bar=100 μm.

One of the many roles of cCas7 is to cleave PARP, a potent inducer of apoptosis, which confirms a fate of death for the cell. Therefore, with evidence demonstrating the activation of cCas7 during SD pathogenesis, the subsequent induction of down-stream apoptotic factors such as cleaved PARP was anticipated. In wildtype hexb$^{+/+}$ spinal cord segments, minimal immunoreactivity toward cleaved PARP was observed with very few cells showing cytosolic staining (FIG. 13 A,C,E). This pattern of immunolabeling was consistent among the different regions of the spinal cord. Interestingly, hexb$^{-/-}$ spinal sections demonstrated increased nuclear staining of cleaved PARP. Nuclear localization of PARP, albeit at minimal levels, was noted as early as 60 d in hexb$^{-/-}$ samples, where a regional specific presentation of nuclear staining was observed (FIG. 13 B). Cervical segments presented minimal staining in total but contained some nuclear labelled AHNs. Conversely, thoracic and lumbar regions also contained multiple AHNs with clear nuclear staining, but the global staining of these regions was augmented in comparison to cervical sections. As SD progressed and accumulations were exacerbated, a sharp increase in total staining was seen within 80 d hexb$^{-/-}$ samples (FIG. 13 D). Interregionally, the staining appeared most abundant within the lumbar segment and more modest in the cervical and thoracic regions. Nuclear staining was also more dispersed throughout the entirety of the lumbar and thoracic sections, differing from cervical which seemed to have much of its staining in the anterior horn, specifically within the AHNs. When evaluated intracellularly, the nuclear abundance of cleaved PARP amongst AHNs was striking. At 100 d hexb$^{-/-}$ samples showed a drastic decrease of cleaved PARP immunoreactivity which was concurrent with the observed decrease in cCas7 (FIG. 13 F).

These results indicate that the activation of cCas7, leading to the cleavage of PARP and the induction of apoptosis, peaks at 60 d of age and tapers down as the SD mouse approaches end point at 120 d of age. In parallel, cleaved PARP showed a similar pattern of decrease overtime but its peak appeared to be at 80 d. Therefore, the conception of this intense activation of two factors which are vital for apoptotic events, indicates that neuronal apoptosis is occurring in the spinal cord at high frequencies as early as 60 d of age in mouse models of Sandhoff disease.

To assess the efficacy of chemical chaperone 4-PBA in reducing ER stress, hexb$^{-/-}$ mice were administered 4-PBA in their drinking water at 40 d of age and underwent behavioral testing beginning at 7 weeks of age. Utilizing several behavioral tests such as wire hang, body weight, and righting response, measures of degeneration of cerebellar and motor neuromuscular functions were collected (FIG. 14). Analyzing motor neural impairment utilizing a wire hang test revealed a significant increase in wire hang time of treated mice in comparison to untreated mice (FIG. 14 B). 4-PBA treated mice showed a more gradual decline indicative of delayed neuromuscular impairment. Furthermore, assessing balance and motor coordination by examining righting response times highlighted that treatment with 4-PBA resulted in a significantly faster righting response within SD mice (FIG. 14 C). Untreated mice suffered a massive increase in righting response time by 17 weeks of age while in contrast, treated mice demonstrated a 2-week delay in righting response time impairment, with faster times being recorded until 19 weeks of age. Additionally, body mass measurement revealed that treatment with 4-PBA restored hexb$^{-/-}$ mice weights to wildtype levels (FIG. 14 A). Lastly, an analysis of survivability was conducted using a Mantel-Cox test (FIG. 14 D). 4-PBA had a beneficial impact on lifespan with a significant difference ($P<0.001$) of survival noted between treated and untreated SD mice. Overall, an increase of 16 days was noted, with 127 days as the median survival age for untreated hexb$^{-/-}$ mice and 143 days for 4-PBA treated hexb$^{-/-}$ mice. These results indicate that 4-PBA functioned to obviate the severity of neuromuscular degeneration in hexb$^{-/-}$ mice and highlighted the therapeutic implications of 4-PBA treatment in SD.

The pharmacological benefits of 4-PBA have been demonstrated on motor neuronal impairment seen in SD mice. UPR activation was assessed through immunofluorescent staining of phosphorylated eukaryotic initiation factor 2 alpha (p-eIF2α) positive neurons and transcription factor YY1 in spinal cord sections from hexb$^{-/-}$ mice that were treated or untreated with 4-PBA for (FIG. 15). Within the spinal samples of untreated SD mice revealed cytosolic p-eIF2a staining within neurons. However, following treatment with 4-PBA, a significant reduction in the number of cytosolic p-eIF2α-positive neurons was observed. The phosphorylation of eIF2α demarcates the presence of ER stress and therefore the loss of cytosolic staining and the presence of less intense nuclear staining following treatment supports the function of 4-PBA in alleviating ER stress. Furthermore, the degree of apoptotic events occurring during disease pathogenesis with and without 4-PBA treatment was evaluated (FIG. 16). Spinal cord sections were double immunostained for cleaved caspase 7-positive neurons and neuronal marker NeuN. Results indicated a significant reduction in the number of cCas7 positive neurons present throughout the spinal cord after 4-PBA treatment. Overall, these results demonstrate that 4-PBA reduces ER stress and as a result decreases cCas7 activation preventing apoptosis with significant beneficial impact on SD pathophysiology.

One of the hall marks of motor neurons within the spinal cord is the enzyme choline acetyltransferase (ChAT). In order to assess the effect of 4-PBA on the integrity of motor neurons i.e., AHNs, the immunostained hexb$^{+/+}$ and hexb$^{-/-}$ spinal section were doubled with anti-ChAT and anti-GFAP antibodies. The results highlighted a significant loss of AHNs motor neurons throughout each segment of the spinal cord of hexb$^{-/-}$ mice as well as significant astrogliosis as noted with increased GFAP staining (FIG. 17). Of particular interest, C-boutons, which are pronounced and notable at synapses in hexb$^{+/+}$ spinal sections, showed massive loss in the hexb$^{-/-}$ spinal sections. However, following treatment with 4-PBA, ChAT staining was normalized, with C-boutons more prevalent around AHNs motor neurons and throughout the anterior horn (FIG. 17). Furthermore, in order to assess the impact of 4-PBA treatment on sensory neurons, spinal sections for Calretinin were stained. The Calretinin-positive interneurons (sensory processing neurons) in hexb$^{-/-}$ spinal section showed more intense staining with some interneurons appearing prominent within the anterior horn region when compared with interneurons in hexb+/+ spinal sections. In contrast, 4-PBA treatment maintained viable AHNs and showed very little Calretinin-positive interneurons within the anterior horn region (FIG. 18).

Neuromuscular deficits are a highly prevalent consequence of Sandhoff disease. Therefore, cell body sectional area of the anterior horn neurons and the cross-sectional area of muscle fibers from the muscles surrounding the spinal cord of 80 d hexb$^{+/+}$ and hexb$^{-/-}$ mice were evaluated (FIG. 19). Within hexb$^{+/+}$ mice, muscle fibres have an average area of ~1000 um$^2$ while in contrast hexb$^{-/-}$ mice show a 44% reduction in area with an average of ~570 um$^2$. Such a drastic reduction early in disease pathology indicates mass muscle atrophy and neuronal loss has already occurred. Following treatment with chemical chaperone 4-PBA, muscle fiber cross-sectional area was found to be within hexb$^{+/+}$ range averaging 900 um$^2$, with no significant difference noted between hexb$^{+/+}$ and 4-PBA treated hexb$^{-/-}$ mice muscle fiber cross section area (FIG. 19 B). A significant difference was observed in skeletal muscles of untreated and treated hexb$^{-/-}$ mice indicating that 4-PBA maintains neuromuscular innervation and reduces muscle atrophy.

DISCUSSION

The spinal cord contributes to all vital physiological functions including movement, breathing, and sensory processing [38, 39]. A hallmark of GM2 gangliosidosis is massive substrate accumulation within lysosomes of neurons throughout the CNS, particularly the spinal cord. Lysosomal lipid accumulation is histologically prominent within the spinal anterior horn motor neurons of hexb$^{-/-}$ mice [13]. This lysosomal accumulation can trigger a wide range of consequences within neurons including lysosomal rupture, ER stress induction, and Ca$^{2+}$ dysregulation with consequences seen throughout the spinal cord, which shows mass amounts of neuronal death. At the terminal stages of the disease, lysosomal storage disrupts the spinal cord cytology and functions. These results demonstrate that hexb$^{-/-}$ AHN show extensive lipid accumulations leading to lysosomal enlargement and overall swelling of the neuron. Here a drastic increase in the size of these anterior horn neuronal cell bodies is reported by 100 and 120 days in hexb$^{-/-}$ spinal cord samples. This lysosomal induced swelling leads to alterations of the intracellular location of the ER, as well as other organelles. This additional disturbance of the ER may potentially exacerbate the overall negative impact this disease has on neuronal survival. The location of affected neurons within the CNS is critical and although neuronal loss is gradual, the overall reduction in AHNs numbers within the spinal cord is expected to have a severe impact on motor neuronal circuitry and motoneuronal function. Circuitry loss may occur in a sequential manner, but further investigation is required to fully uncover this pathological process. An about 50% reduction in hexb$^{-/-}$ AHN abundance was also observed throughout the entirety of the spinal cord by the terminal stage of the disease (120 days). These morphological changes in combination with the loss of AHNs in hexb$^{-/-}$ mice parallels the phenotypic onset observed around 100 days. Initial symptoms include impairment of motor function involving balance and coordination defects which are directly related to AHNs and their normal functioning. As accumulations worsen and depletion of AHNs continues, these symptoms quickly escalate into severe muscle wasting, limited ability to move limbs, and extreme tremors until shortly after the mice succumb to the detrimental consequences of this lipid storage and neuronal loss. Similar trends have been clinically reported in patients with late-onset TSD and SD. Late on-set SD has been described as showing strong similarities in symptomology to that seen in lower motor neuron disease. Examination of these patients reveals distended neurons and widespread denervation within the anterior horn of the spinal cord. Several clinical reports have also highlighted the marked neuronal loss that occurs during disease pathogenesis within the anterior horn of the spinal cord specifically [10]. The location of neuronal loss functionally correlates to the phenotypic outcome seen in these patients, which is gait disturbances, severe muscle weakness, muscle atrophy, fasciculations, and tremors [2]. Although a highly reported phenomenon, the exact mechanism of how the initial insult of accumulation in GM2 gangloisidoses leads to the stark depletion of AHNs. The results from this study provides a further understanding of disease pathogenesis and progression.

In GM2 gangliosidoses, the connection between lipid accumulation within lysosomes and neuronal cell death, which translates into dire clinical outcome seen in patients, is still not completely understood. The examination of ER stress markers provides a potential pathway connecting the enzymatic deficiency and lysosomal storage to an apoptotic outcome. The results highlighted a multitude of ER stress markers that are differentially upregulated temporally throughout the regions of the spinal cord. They also uncovered great diversity in the interregional localization patterns, striking changes in cellular localization, neuronal cell loss, morphological changes, and apoptosis.

The ER has been at the center of several studies which attempted to highlight a mechanistic pathway within several lysosomal storage disorders. Pelled and colleagues (2003) examined the implications of GM2 accumulation in neuronal tissue collected from hexb$^{-/-}$ mice. They were able to identify a causal relationship between the intercellular accumulation of GM2 and rates of $Ca^{2+}$ uptake via the sarco/endoplasmic reticulum $Ca^{2+}$ ATPase (SERCA). In microsomes collected from hexb$^{-/-}$ mice brains, there was a severely diminished $Ca^{2+}$ uptake via SERCA into the ER [18]. Depleted internal $Ca^{2+}$ stores of the ER thereby disrupting $Ca^{2+}$ homeostasis, is highly likely to induce ER stress. In addition, Virgolini et al, also suggested that a depletion of ER $Ca^{2+}$ stores and activation of PERK can be caused by GM2 accumulation within neurons [35]. Although these results appear to support the notion of involvement of ER stress after GM2 accumulation, the study used cell culture of cell lines that were differentiated and then exposed to high concentrations (2 µM) of exogenous GM2; the authors attempted to mimic substrate accumulation by addition of GM2 gangliosides in culture media [35]. Gangliosides cluster at the cell membrane where they are capable of interaction with membrane proteins to modulate a variety of cellular functions such as cell-cell recognition, phenotypic changes, cell growth, and signal transduction [40, 41]. When ganglioside levels are altered, it can lead to reduced membrane fluidity which negatively impacts the cell and generates cellular dysfunction [42]. In Virgolini's study, the addition of GM2 exogenously creates an alteration in ganglioside levels and may result in cellular stress independent of substrate accumulation. This approach causes additional accumulation, independent of β-hexosaminidase deficiency associated with SD. The study failed to account for significant physiological differences between cell cultures and primary neurons from SD models. Therefore, despite the promising results suggesting ER stress involvement, the relevance of these findings is brought into question due to the improper representation of the substrate accumulation that is central to the disease.

Similar studies have been conducted where primary neurons were isolated from a different lysosomal storage mouse model to evaluate the effects of substrate accumulation. The D'azzo group released a study where they determined that through GM1 accumulation in spinal neurons from 3-galactosidase knockout, ER $Ca^{2+}$ was disrupted because of buildup of gangliosides within the ER [31]. They also reported upregulation of CHOP within these neurons which coincided with severe neuropathological symptoms and neuronal loss. Despite the focus of this paper being GM1 gangliosidosis, this research provides strong evidence for ER stress involvement when ganglioside accumulation occurs within neurons. The present application has shown strong indicators for ER stress activation following GM2 accumulation within AHNs of hexb$^{-/-}$ mice. A separate study by Kobolak and colleagues utilized a disease-specific induced pluripotent stem cell (iPSC) line representative of mucopolysaccharidosis II (MPS II) to evaluate disease related neuropathy [32]. These cells were differentiated into neuronal progenitor cells (NPCs) and then terminally differentiated towards cortical neurons. Although this study didn't specifically assess role of ER stress, they were able to identify an increase in expression of cleaved caspase 7, an executioner for apoptotic events, within the diseased cell line when compared to the control [32]. Therefore, this provided evidence of increased apoptotic activity occurring within neurons of LSD patients. Incidentally, there are several studies that reported cCas7 upregulation in ALS patients which could be used to extrapolate a potential common mediator of LMN disease symptoms seen between these disorders [43, 44].

Current evidence highlights the potential role of ER stress, due to ganglioside accumulation or $Ca^{2+}$ dysregulation, in neurodegenerative lysosomal storage diseases, but fails to identify a connecting mechanism of how apoptosis occurs. The results of the present application document multiple activated UPR markers which are potential mediators of apoptosis. Early induction of UPR related factors, ATF6 and XBP1, was identified as early as 60 d. It was also noted that ATF6 was retained within the ER/Golgi at 60 d but by 80 d demonstrated a translocation to the nucleus and a subsequent decrease in its overall expression. GRP78 also exhibited variations in its intracellular localization and expression patterns, with what appeared to be a reduction in overall expression and relocalization to the cell surface occurring between 60 and 80 d. In addition, CHOP, cleaved caspase 7, and cleaved PARP were identified as potential mediators of neuronal death. All three of these factors were clearly activated starting at 60 days and had peaks ranging between 60 and 100 days, which aligned with the most intense levels of neuronal loss observed. Collectively, the subsequent activation of each of these markers and their peaks parallels the initial symptom onset period of 80-100 d seen in hexb$^{-/-}$ mice. At 100 d, the findings showed an initial decrease in neuron numbers which was succeeded by significant activation of both CHOP and c-Cas7 which ultimately intersects with when mice begin to display muscle weakness, tremors, and coordination defects. This indicates these factors are playing a significant role in neurodegeneration and at 100 d or slightly prior, there is an accelerated rate of apoptotic events. The present application evaluated a specific and affected group of neurons. By evaluating the spinal cord spatially and temporally, both neuronal morphological variations and neuronal loss were demonstrated, as well as an induction of multiple mechanistic pathways that connect ER stress activation with mediators of apoptosis. Additionally, these results highlight the early stimulation of these factors at 60 d of age, which is much earlier than expected and emphasized the importance of early therapeutic intervention.

SD and TSD, while differing in enzymatic deficiencies, present with virtually identical phenotypes in humans. The hexb$^{-/-}$ mouse model not only accurately mirrors the progression of SD but is also representative of TSD seen in humans. These results therefore are also relevant to the Tay Sachs disease. These discoveries may also be extended to various other types of lysosomal storage diseases. Overall, the relevancy of these results may extend far beyond the current disease of interest which would allow for significant advances in the mechanistic unravelling of several detrimental diseases and therapeutic innovations.

Many UPR pathway components can play multiple roles throughout the initiation and subsequent activation of downstream cascades depending on a multitude of factors such as the length and intensity of ER stress as well as cell type [45]. One of the factors whose net outcome on the cell is still being debated is ATF6. The role of ATF6 is still not completely understood but most research surrounding it has delved into its role as a pro-survival factor. ATF6 has been observed exhibiting a pro-survival role in response to chronic, yet mild ER stress [46]. Other studies have demonstrated its vital protective role through targeted downregulation of ATF6 which resulted in increased melanoma cellular sensitivity to ER stress inducers, thapsigargin and tunicamycin [46, 47]. The literature reports ATF6 as a pro-survival factor that works to counteract ER stress activation by upregulating ER chaperones, such as GRP78, and XBP1 to improve the efficiency of protesostasis [48]. Contrastingly, some studies have also highlighted the roles of ATF6 in the apoptotic events induced by ER stress. In vascular endothelial cells, high expression of activated ATF6 was observed to exacerbate ER stress-induced apoptosis [45] Conversely, ATF6 has been shown to activate and up-regulate the expression of a multitude of apoptosis invoking factors, such as CHOP and cleaved caspase 9, but it can also trigger inflammation through induction of the NF-kB pathway [45, 49, 50]. Ultimately, current results questioned the true role of ATF6 in SD and which cascade it activates: pro-survival or pro-apoptotic. After 4-PBA treatment, upregulation of ATF6 was observed, which supports its potential pro-survival role. On the other hand, 4-PBA suppressed c-Cas7 which prevented the cleavage of PARP, resulting in motor neuron survival [45, 51, 52]. Although the relationship isn't completely clear, c-Cas7 activation and ATF6 activation seen in SD provide a potential mechanistic pathway connecting ER stress to neurodegeneration. Overall, these results emphasize key markers of ER stress and apoptosis that could be evaluated as therapeutic targets in future studies.

Interestingly, these results also indicated a highly specific localization pattern and expression levels of GRP78. It's been highly recognized that GRP78 becomes upregulated during ER stress through means of all three arms of the UPR and functions as an ER chaperone protein to help reduce the load of unfolded proteins accumulating within the ER [48, 50, 53]. These results suggest differential GRP78 expression accompanied by localization to the cell membrane. Within the spinal cords of SD mice, neurons exhibiting localization of GRP78 to the cell membrane were observed. This redistribution isn't a novel finding in that there have been multiple reports of GRP78 sequestration at the cell surface, which is actively promoted by ER stress, where it functions to regulate processes such as proliferation, inflammation, and apoptosis [54, 55]. However, the relationship between localization and SD pathogenesis and its initiation early in disease progression may be a protective response leading to a decrease in ER stress and neurodegeneration while others report a potential connection to apoptosis [45, 48, 56]. Another interesting aspect of these results is the apparent decrease in GRP78 expression in hexb$^{-/-}$ spinal cord samples throughout disease advancement in comparison to hexb$^{+/+}$ samples. Albeit this could be due to the drastic change in intracellular localization because of ER stress activation and disruptions in cellular morphology, a consequence of lysosomal accumulation, this variation has the potential to result in induction of proapoptotic cascades involving various caspases. Of particular interest, it has been observed that increased expression of GRP78 promoted by ER stress, is capable of binding to caspase 7, suppressing its activation [55, 57]. The expression levels and cellular localization could provide evidence of a potential secondary apoptotic cascade. Along the same lines, downregulation of GRP78 has been correlated with an increase in the expression of multiple caspases, including caspase 7 [58]. Within this model it could be suggested that a down regulation in GRP78 during SD and its subsequent redistribution throughout the cell and to the cell membrane could result in a diminished ability to bind caspase 7 therefore allowing for activation and initiation of caspase 7's apoptotic cascade. This research provides data which supports this notion in that a reduction of GRP78 immunohistological expression in hexb$^{-/-}$ samples beginning at 60 days was observed. This tapering aligns with the peak of nuclear c-Cas7 positive cells in the anterior horn of hexb$^{-/-}$ samples. However, there are other potential mechanisms that could result in the consequential activation of caspase 7, independently of ER stress factors [51].

The uncovering of mechanistic pathways involved in SD development and advancement provide promising data identifying many factors as potential therapeutic targets.

Further studies using hexb Cas7 double knockout mouse models may help determine the role of several factors that contribute significantly to the neurodegenerative process in the disease. Since caspase 7 is intricately involved in the molecular mechanisms of SD pathogenesis, caspase 7 knockout mouse which presents with a normal phenotype, could be an ideal model for the generation of Cas7$^{-/-}$ hexb$^{-/-}$ mice. Another possibility is the generation of a chop$^{-/-}$ hexb$^{-/-}$ mouse, in hopes of preventing apoptosis initiation and subsequent neuronal loss. Both double knockout mouse models could shed significant light on the roles of the Cas7 and CHOP during Sandhoff disease progression.

This work highlights significant changes in morphological features of anterior horn neurons as well as severe neuronal loss of about 50% in the spinal cord by the terminal stages of SD in hexb$^{-/-}$ mice. It was also established that differential immunohistochemical localization and expression levels of ATF6, XBP1, Grp78, CHOP, cCas7 and cleaved PARP between hexb$^{-/-}$ and hexb$^{+/+}$ spinal cord sections. cCas7 and CHOP showed irrefutable upregulation, with their peak expression occurring between 60 d and 80 d. Evidence demonstrating that ER stress induction and apoptotic events occur considerably earlier in the timeline of disease progression, around 80 d. The ER is emerging as a vital regulator of cell fate and apoptosis, and these findings present ER stress and the UPR, as well as subsequent activation of potent inducers of apoptosis, as novel mechanistic pathways involved in SD pathogenesis. Furthermore, these studies have demonstrated that a chemical chaperone 4-PBA can obviate the severity and consequences of ER stress in Sandhoff disease mice. The drug was administered in drinking water starting at 40 d of age and observed a significant improvement in motor neuromuscular function and life span in SD mice.

The results indicate dynamic changes in the number and localization of calretinin-expressing interneurons as well as ChAT-positive motor neurons in the spinal cord of hexb$^{-/-}$ mice. This suggests that interneuron networks which often relay signals to coordinate between sensory and motor neurons might be altered in the spinal cord of hexb-/- mice resulting among other things in altered sensory thresholds. In fact, Smith et al has demonstrated that activation of Calretinin-positive interneurons in vivo caused enhanced pain sensation. The positive impact of 4-PBA treatment on the numbers of ChAT-positive motor neurons and Calretinin-positive interneurons within the anterior horn regions may suggest that 4-PBA restores not only motor function but also sensory threshold. 4-PBA appears to suppress disease-associated neuromuscular deficiencies and pain [59].

Based on these results, 4-PBA and other compounds that can mitigate ER stress, emerge as therapeutic drugs for the treatment of Sandhoff disease and other related lysosomal storage disorders. Overall, this discovery provides strong evidence for the role of chronic ER stress and UPR activation in the spine pathophysiology of Sandhoff disease. Therefore, these observations can be extended to these other neurodegenerative disorders, where motor neuron loss is highly significant.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

1. Sun, A., et al., Lysosomal Storage Disorders, in Emery and Rimoin's Principles and Practice of Medical Genetics and Genomics. 2021, Elsevier. p. 563-682.
2. Jamrozik, Z., et al., Late onset GM2 gangliosidosis mimicking spinal muscular atrophy. Gene, 2013. 527(2): p. 679-82.
3. Delnooz, C. C., et al., New cases of adult-onset Sandhoff disease with a cerebellar or lower motor neuron phenotype. J Neurol Neurosurg Psychiatry, 2010. 81(9): p. 968-72.
4. Yokoyama, M., E. G. Trams, and R. O. Brady, Sphingolipid antibodies in sera of animals and patients with central nervous system lesions. Proc Soc Exp Biol Med, 1962. 111: p. 350-2.
5. Kohno, Y., et al., [Adult Sandhoff disease presented as a motor neuron disease phenotype with slow progression]. Rinsho Shinkeigaku, 2001. 41(1): p. 36-9.
6. Takado, Y., et al., [A patient with GM2 gangliosidosis presenting with motor neuron disease symptom in his forties]. Rinsho Shinkeigaku, 2007. 47(1): p. 3741.
7. Khoueiry, M., E. Malek, and J. S. Salameh, Adult onset Sandhoff disease: a rare mimicker of amyotrophic lateral sclerosis. Amyotroph Lateral Scler Frontotemporal Degener, 2020. 21(1-2): p. 144-146.
8. Alonso-Perez, J., et al., Late onset Sandhoff disease presenting with lower motor neuron disease and stuttering. Neuromuscular Disorders, 2021.
9. Shibuya, M., et al., A 23-year follow-up report of juvenile-onset Sandhoff disease presenting with a motor neuron disease phenotype and a novel variant. Brain Dev, 2021. 43(10): p. 1029-1032.
10. Yokoyama, T., et al., Late onset GM2 gangliosidosis presenting with motor neuron disease: an autopsy case. Neuropathology, 2014. 34(3): p. 304-8.
11. Scarpelli, M., et al., Natural history of motor neuron disease in adult onset GM2gangliosidosis: A case report with 25 years of follow-up. Mol Genet Metab Rep, 2014. 1: p. 269-272.
12. Huang, J. Q., et al., Apoptotic cell death in mouse models of GM2 gangliosidosis and observations on human Tay-Sachs and Sandhoff diseases. Hum Mol Genet, 1997. 6(11): p. 1879-85.
13. Sango, K., et al., Mouse models of Tay-Sachs and Sandhoff diseases differ in neurologic phenotype and ganglioside metabolism. Nat Genet, 1995. 11(2): p. 170-6.
14. Phaneuf, D., et al., Dramatically different phenotypes in mouse models of human TaySachs and Sandhoff diseases. Hum Mol Genet, 1996. 5(1): p. 1-14.
15. Holzer, H. T., et al., Cerebellar atrophy on top of motor neuron compromise as indicator of late-onset GM2 gangliosidosis. J Neurol, 2021.
16. Schnorf, H., et al., Early and severe sensory loss in three adult siblings with hexosaminidase A and B deficiency (Sandhoff disease). J Neurol Neurosurg Psychiatry, 1995. 59(5): p. 520-3.
17. Bellettato, C. M. and M. Scarpa, Pathophysiology of neuropathic lysosomal storage disorders. J Inherit Metab Dis, 2010. 33(4): p. 347-62.
18. Pelled, D., et al., Inhibition of calcium uptake via the sarco/endoplasmic reticulum Ca2+ATPase in a mouse model of Sandhoff disease and prevention by treatment with Nbutyldeoxynojirimycin. J Biol Chem, 2003. 278 (32): p. 29496501.
19. Bosch, M. E. and T. Kielian, Neuroinflammatory paradigms in lysosomal storage diseases. Front Neurosci, 2015. 9: p. 417.
20. Tessitore, A., et al., GM1-ganglioside-mediated activation of the unfolded protein response causes neuronal death in a neurodegenerative gangliosidosis. Mol Cell, 2004. 15(5): p. 753-66.
21. Abo-Ouf, H., et al., Deletion of tumor necrosis factor-alpha ameliorates neurodegeneration in Sandhoff disease mice. Hum Mol Genet, 2013. 22(19): p. 3960-75.
22. Wada, R., C. J. Tifft, and R. L. Proia, Microglial activation precedes acute neurodegeneration in Sandhoff disease and is suppressed by bone marrow transplantation. Proc Natl Acad Sci USA, 2000. 97(20): p. 10954-9.

23. Adams, C. J., et al., Structure and Molecular Mechanism of ER Stress Signaling by the Unfolded Protein Response Signal Activator IRE1. Front Mol Biosci, 2019. 6: p. 11.
24. Lu, M., et al., The structure and global distribution of the endoplasmic reticulum network are actively regulated by lysosomes. Sci. Adv, 2020. 6(51).
25. Phillips, M. J. and G. K. Voeltz, Structure and function of ER membrane contact sites with other organelles. Nat Rev Mol Cell Biol, 2016. 17(2): p. 69-82.
26. Giamogante, F., et al., ER-Mitochondria Contact Sites Reporters: Strengths and Weaknesses of the Available Approaches. Int J Mol Sci, 2020. 21(21).
27. Annunziata, I. and A. d'Azzo, Interorganellar membrane microdomains: dynamic platforms in the control of calcium signaling and apoptosis. Cells, 2013. 2(3): p. 574-90.
28. Burgoyne, T., S. Patel, and E. R. Eden, Calcium signaling at ER membrane contact sites. Biochim Biophys Acta, 2015. 1853(9): p. 2012-7.
29. Scorrano, L., et al., Coming together to define membrane contact sites. Nat Commun, 2019. 10(1): p. 1287.
30. Wu, H., P. Carvalho, and G. K. Voeltz, Here, there, and everywhere: The importance of ER membrane contact sites. Science, 2018. 361(6401).
31. Tessitore, A., et al., GM1-ganglioside-mediated activation of the unfolded protein response causes neuronal death in a neurodegenerative gangliosidosis. Mol Cell, 2004. 15(5): p. 753-66.
32. Kobolak, J., et al., Modelling the neuropathology of lysosomal storage disorders through disease-specific human induced pluripotent stem cells. Exp Cell Res, 2019. 380(2): p. 216233.
33. Sano, R., et al., GM1-ganglioside accumulation at the mitochondria-associated ER membranes links ER stress to Ca(2+)-dependent mitochondrial apoptosis. Mol Cell, 2009. 36(3): p. 500-11.
34. d'Azzo, A., A. Tessitore, and R. Sano, Gangliosides as apoptotic signals in ER stress response. Cell Death Differ, 2006. 13(3): p. 404-14.
35. Virgolini, M. J., et al., Neurite atrophy and apoptosis mediated by PERK signaling after accumulation of GM2-ganglioside. Biochim Biophys Acta Mol Cell Res, 2019. 1866(2): p. 225-239.
36. Wei, H., et al., ER and oxidative stresses are common mediators of apoptosis in both neurodegenerative and non-neurodegenerative lysosomal storage disorders and are alleviated by chemical chaperones. Hum Mol Genet, 2008. 17(4): p. 46977.
37. Ballabio, A. and J. S. Bonifacino, Lysosomes as dynamic regulators of cell and organismal homeostasis. Nat Rev Mol Cell Biol, 2020. 21(2): p. 101-118.
38. Felten, D. L. and A. Shetty, Netter's Atlas of Neuroscience E-Book: with STUDENT CONSULT Online Access. 2011: Elsevier Health Sciences.
39. Bican, O., A. Minagar, and A. A. Pruitt, The spinal cord: a review of functional neuroanatomy. Neurol Clin, 2013. 31(1): p. 1-18.
40. Hakomori, S., Organization and function of glycosphingolipids in membrane. Proceedings of the Japan Academy, Series B, 2005. 81(6): p. 189-203.
41. Regina Todeschini, A. and S. I. Hakomori, Functional role of glycosphingolipids and gangliosides in control of cell adhesion, motility, and growth, through glycosynaptic microdomains. Biochim Biophys Acta, 2008. 1780(3): p. 421-33.
42. Sasaki, N., et al., Ganglioside GM2, highly expressed in the MIA PaCa-2 pancreatic ductal adenocarcinoma cell line, is correlated with growth, invasion, and advanced stage. Sci Rep, 2019. 9(1): p. 19369.
43. Guegan, C. and S. Przedborski, Programmed cell death in arnyotrophic lateral sclerosis. J Clin Invest, 2003. 111(2): p. 153-61.
44. Li, Q., et al., The cleavage pattern of TDP-43 determines its rate of clearance and cytotoxicity. Nat Commun, 2015. 6: p. 6183.
45. Huang, J., et al., High expression of active ATF6 aggravates endoplasmic reticulum stress-induced vascular endothelial cell apoptosis through the mitochondrial apoptotic pathway. Mol Med Rep, 2018. 17(5): p. 6483-6489.
46. Lindner, P., et al., Cell death induced by the ER stressor thapsigargin involves death receptor 5, a non-autophagic function of MAP1 LC3B, and distinct contributions from unfolded protein response components. Cell Commun Signal, 2020. 18(1): p. 12.
47. Tay, K. H., et al., Sustained IRE1 and ATF6 signaling is important for survival of melanoma cells undergoing ER stress. Cell Signal, 2014. 26(2): p. 287-94.
48. Hillary, R. F. and U. FitzGerald, A lifetime of stress: ATF6 in development and homeostasis. J Biomed Sci, 2018. 25(1): p. 48.
49. Sharma, R. B., J. T. Snyder, and L. C. Alonso, Atf6a impacts cell number by influencing survival, death and proliferation. Mol Metab, 2019. 27S: p. S69-S80.
50. Yang, H., et al., ATF6 Is a Critical Determinant of CHOP Dynamics during the Unfolded Protein Response. iScience, 2020. 23(2): p. 100860.
51. Lamkanfi, M. and T. D. Kanneganti, Caspase-7: a protease involved in apoptosis and inflammation. Int J Biochem Cell Biol, 2010. 42(1): p. 21-4.
52. Brentnall, M., et al., Caspase-9, caspase-3 and caspase-7 have distinct roles during intrinsic apoptosis. BMC Cell Biol, 2013. 14: p. 32.
53. Wang, M., et al., Role of the unfolded protein response regulator GRP78/BiP in development, cancer, and neurological disorders. Antioxid Redox Signal, 2009. 11(9): p. 2307-16.
54. Zhang, Y., et al., Cell surface relocalization of the endoplasmic reticulum chaperone and unfolded protein response regulator GRP78/BiP. J Biol Chem, 2010. 285 (20): p. 1506515075.
55. Lee, A. S., Glucose-regulated proteins in cancer: molecular mechanisms and therapeutic potential. Nat Rev Cancer, 2014. 14(4): p. 263-76.
56. Louessard, M., et al., Activation of cell surface GRP78 decreases endoplasmic reticulum stress and neuronal death. Cell Death Differ, 2017. 24(9): p. 15181529.
57. Reddy, R. K., et al., Endoplasmic reticulum chaperone protein GRP78 protects cells from apoptosis induced by topoisomerase inhibitors: role of ATP binding site in suppression of caspase-7 activation. J Biol Chem, 2003. 278(23): p. 20915-24.
58. Liu, Y., et al., Downregulation of GRP78 and XIAP is correlated with apoptosis during cerulein-induced acute pancreatitis in rats via regulation of caspase activation. Mol Med Rep, 2013. 7(3): p. 725-30.
59. Smith, K. M. et al., Calretinin positive neurons form an excitatory amplifier network in the spinal cord dorsal horn. ELife, 2019. 8: p. 1-32.
60. Pereira, D, M. et al, Tuning protein folding in lysosomal storage diseases: the chemistry behind pharmacological chaperones. Chem. Sci, 2018, 9, 1740.
61. Wei, H. et al, ER and oxidative stresses are common mediators of apoptosis in both neurodegenerative and non-neurodegenerative lysosomal storage disorders and are alleviated by chemical chaperones. Hum Mol Genet. 2018, 17(4), 469-477.

The invention claimed is:

1. A method of treating Sandhoff Disease (SD) comprising administering a therapeutically effective amount of 4-phenylbutyric acid (4-PBA), or a pharmaceutically acceptable salt, co-crystal, polymorph and/or solvate thereof, to a subject in need thereof, wherein the method treats neurodegenerative symptoms of SD and the neurodegenerative symptoms are symptoms arising from degeneration of lower motor neurons, wherein the symptoms comprise peripheral neuropathy and/or motor neuromuscular weakness.

2. The method of claim 1, wherein the SD is selected from infantile, juvenile, and late-onset forms.

3. The method of claim 2, wherein the SD is a late-onset form.

4. The method of claim 1, wherein the method achieves at least one of delayed neurological symptoms, reduced pain, improved motor neuromuscular function or increased life span.

5. The method of claim 1, wherein 4-PBA or the pharmaceutically acceptable salt, co-crystal, polymorph and/or solvate thereof, modulates a target that is selected from one or more of the following: glial fibrillary acidic protein (GFAP), activating transcription factor 6 (ATF6), XBP1 (X-Box binding protein 1), glucose regulatory protein 78 (Grp78), IRE1-phos, homologous protein (CHOP), protein disulfide isomerase (PDI), caspase 7, poly (ADP-ribose) polymerase (PARP) and CCAAT/enhancer-binding protein (C/EBP).

6. The method of claim 1, wherein the method comprises reduction in the number of cytosolic p-eIF2α-positive neurons in a spinal cord of the subject.

7. The method of claim 1, wherein the method comprises reduction in the number of cCas7 positive neurons in a spinal cord of the subject.

8. The method of claim 1, wherein the method comprises maintaining the activity of the enzyme choline acetyltransferase (ChAT).

9. The method of claim 1, wherein the method comprises reduction in calretinin-positive interneurons.

10. The method of claim 1, wherein the method comprises maintaining muscle myofibril integrity.

11. The method of claim 1, wherein the subject is human.

12. The method of claim 1, wherein 4-PBA is administered orally.

13. The method of claim 1, wherein 4-PBA is administered in a liquid dosage form.

14. The method of claim 1, wherein 4-PBA is administered at a dose ranging from about 0.1 g/kg body weight/day to about 10 g/kg body weight/day.

15. The method of claim 1, wherein the method further comprises administering a second therapeutic agent for treatment of lysosomal storage diseases.

16. The method of claim 1, wherein the symptoms further comprise impaired balance, impaired motor coordination, gait disturbances, muscle weakness, muscle atrophy, fasciculations, and/or tremors.

* * * * *

SEQUENCE LISTING

```
Sequence total quantity: 3
SEQ ID NO: 1            moltype = DNA   length = 24
FEATURE                 Location/Qualifiers
source                  1..24
                        mol_type = other DNA
                        organism = synthetic construct
SEQUENCE: 1
ggtttctaca agagacatca tggc                                              24

SEQ ID NO: 2            moltype = DNA   length = 24
FEATURE                 Location/Qualifiers
source                  1..24
                        mol_type = other DNA
                        organism = synthetic construct
SEQUENCE: 2
gatattgctg aagagcttgg cggc                                              24

SEQ ID NO: 3            moltype = DNA   length = 24
FEATURE                 Location/Qualifiers
source                  1..24
                        mol_type = other DNA
                        organism = synthetic construct
SEQUENCE: 3
caatcggtgc ttacaggttt catc                                              24
```